US011046785B2

(12) United States Patent
Conley et al.

(10) Patent No.: US 11,046,785 B2
(45) Date of Patent: Jun. 29, 2021

(54) COMPOSITIONS AND METHODS FOR TREATMENT OF DIABETIC MACULAR EDEMA

(71) Applicant: Dyax Corp., Lexington, MA (US)

(72) Inventors: Gregory P. Conley, Arlington, MA (US); Andrew Nixon, Hanover, MA (US); Daniel J. Sexton, Melrose, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/541,743

(22) Filed: Aug. 15, 2019

(65) Prior Publication Data

US 2020/0115469 A1   Apr. 16, 2020

Related U.S. Application Data

(63) Continuation of application No. 14/669,607, filed on Mar. 26, 2015, now Pat. No. 10,428,158.

(60) Provisional application No. 61/971,170, filed on Mar. 27, 2014.

(51) Int. Cl.
| | | |
|---|---|---|
| A61K 39/00 | (2006.01) | |
| C07K 16/40 | (2006.01) | |
| A61P 27/02 | (2006.01) | |
| A61K 9/00 | (2006.01) | |

(52) U.S. Cl.
CPC ............ *C07K 16/40* (2013.01); *A61P 27/02* (2018.01); *A61K 9/0051* (2013.01); *A61K 2039/505* (2013.01); *A61K 2039/54* (2013.01); *C07K 2317/30* (2013.01); *C07K 2317/55* (2013.01); *C07K 2317/76* (2013.01); *C07K 2317/92* (2013.01)

(58) Field of Classification Search
CPC   C07K 16/40; C07K 2317/76; C07K 2317/55; A61P 27/02; A61K 2039/54
See application file for complete search history.

(56) References Cited

U.S. PATENT DOCUMENTS

| | | |
|---|---|---|
| 3,682,776 A | 8/1972 | Grundmann et al. |
| 3,691,016 A | 9/1972 | Patel |
| 3,969,287 A | 7/1976 | Jaworek et al. |
| 4,118,481 A | 10/1978 | Schnabel et al. |
| 4,153,687 A | 5/1979 | Schnabel et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,377,572 A | 3/1983 | Schwarz et al. |
| 4,399,216 A | 8/1983 | Axel et al. |
| 4,447,224 A | 5/1984 | Decant |
| 4,447,233 A | 5/1984 | Mayfield |
| 4,595,674 A | 6/1986 | Tschesche et al. |
| 4,609,725 A | 9/1986 | Brady et al. |
| 4,634,665 A | 1/1987 | Axel et al. |
| 4,657,893 A | 4/1987 | Krantz et al. |
| 4,845,242 A | 7/1989 | Powers et al. |
| 4,881,175 A | 11/1989 | Ladner |
| 4,931,385 A | 6/1990 | Block et al. |
| 4,946,778 A | 8/1990 | Ladner et al. |
| 4,966,852 A | 10/1990 | Wun et al. |
| 5,045,452 A | 9/1991 | Spragg et al. |
| 5,106,833 A | 4/1992 | Broze, Jr. et al. |
| 5,118,668 A | 6/1992 | Auerswald et al. |
| 5,166,133 A | 11/1992 | Houston et al. |
| 5,179,017 A | 1/1993 | Axel et al. |
| 5,187,153 A | 2/1993 | Cordell et al. |
| 5,212,091 A | 5/1993 | Diaz-Collier et al. |
| 5,217,951 A | 6/1993 | Lezdey et al. |
| 5,223,409 A | 6/1993 | Ladner et al. |
| 5,260,203 A | 11/1993 | Ladner et al. |
| 5,278,144 A | 1/1994 | Wolf |
| 5,278,285 A | 1/1994 | Ebbers et al. |
| 5,312,736 A | 5/1994 | Rasmussen et al. |
| 5,372,933 A | 12/1994 | Zamarron et al. |
| 5,373,090 A | 12/1994 | Norris et al. |
| 5,378,614 A | 1/1995 | Petersen et al. |
| 5,407,915 A | 4/1995 | Fritz et al. |
| 5,409,895 A | 4/1995 | Morishita et al. |
| 5,426,224 A | 6/1995 | Lee et al. |
| 5,441,931 A | 8/1995 | Sprecher et al. |
| 5,444,156 A | 8/1995 | Veloso et al. |
| 5,446,090 A | 8/1995 | Harris |
| 5,455,338 A | 10/1995 | Sprecher et al. |
| 5,466,783 A | 11/1995 | Wun et al. |

(Continued)

FOREIGN PATENT DOCUMENTS

| | | |
|---|---|---|
| BR | 112015017195 A2 | 7/2017 |
| CN | 1233256 A | 10/1999 |

(Continued)

OTHER PUBLICATIONS

[No Author Listed] Dyax's DX-2930 granted Orphan Drug designation in hereditary angioedema. Dec. 6, 2013. [No Author Listed] Fair Disclosure Wire, "Dyax Corp. announces positive results from phase 1a clinical trial of DX2930" dated Feb. 25, 2014. Last accessed from http://dialog.proquest.com/professional/printviewfile?accountid=157282 on May 20, 2016. p. 1-15.

(Continued)

*Primary Examiner* — Lei Yao
(74) *Attorney, Agent, or Firm* — Wolf, Greenfield & Sacks, P.C.

(57) ABSTRACT

Disclosed herein are compositions comprising one or more antibodies that specifically bind active plasma kallikrein (e.g., human plasma kallikrein) and methods of using such compositions for the treatment of retinal diseases, such as diabetic macular edema.

7 Claims, 15 Drawing Sheets

Specification includes a Sequence Listing.

(56) References Cited

U.S. PATENT DOCUMENTS

| | | |
|---|---|---|
| 5,563,123 A | 10/1996 | Innis et al. |
| 5,576,294 A | 11/1996 | Norris et al. |
| 5,583,107 A | 12/1996 | Wolf et al. |
| 5,585,089 A | 12/1996 | Queen et al. |
| 5,589,359 A | 12/1996 | Innis et al. |
| 5,618,696 A | 4/1997 | Norris et al. |
| 5,629,176 A | 5/1997 | Bjørn et al. |
| 5,635,187 A | 6/1997 | Bathurst et al. |
| 5,648,331 A | 7/1997 | Koudsi et al. |
| 5,663,143 A | 9/1997 | Ley et al. |
| 5,672,662 A | 9/1997 | Harris et al. |
| 5,677,146 A | 10/1997 | Sprecher et al. |
| 5,693,761 A | 12/1997 | Queen et al. |
| 5,693,762 A | 12/1997 | Queen et al. |
| 5,695,760 A | 12/1997 | Faanes et al. |
| 5,696,088 A | 12/1997 | Innis et al. |
| 5,719,041 A | 2/1998 | Lazarus et al. |
| 5,736,364 A | 4/1998 | Kelley et al. |
| 5,739,208 A | 4/1998 | Harris |
| 5,747,449 A | 5/1998 | Lasters et al. |
| 5,770,568 A | 6/1998 | Auerswald et al. |
| 5,780,265 A | 7/1998 | Dennis et al. |
| 5,786,328 A | 7/1998 | Dennis et al. |
| 5,795,865 A | 8/1998 | Markland et al. |
| 5,795,954 A | 8/1998 | Lazarus et al. |
| 5,800,385 A | 9/1998 | Demopulos et al. |
| 5,804,376 A | 9/1998 | Braxton et al. |
| 5,824,870 A | 10/1998 | Braszczynski et al. |
| 5,834,244 A | 11/1998 | Dennis et al. |
| 5,843,895 A | 12/1998 | Lazarus et al. |
| 5,849,992 A | 12/1998 | Meade et al. |
| 5,853,723 A | 12/1998 | Jacobs et al. |
| 5,863,893 A | 1/1999 | Dennis et al. |
| 5,869,637 A | 2/1999 | Au-Young et al. |
| 5,874,407 A | 2/1999 | Kelley et al. |
| 5,880,256 A | 3/1999 | Dennis et al. |
| 5,900,461 A | 5/1999 | Harris |
| 5,914,316 A | 6/1999 | Brown et al. |
| 5,932,462 A | 8/1999 | Harris et al. |
| 5,951,974 A | 9/1999 | Gilbert et al. |
| 5,962,266 A | 10/1999 | White et al. |
| 5,990,237 A | 11/1999 | Bentley et al. |
| 5,994,125 A | 11/1999 | Markland et al. |
| 6,001,596 A | 12/1999 | Hillman et al. |
| 6,004,579 A | 12/1999 | Bathurst et al. |
| 6,008,196 A | 12/1999 | Curran et al. |
| 6,010,880 A | 1/2000 | Markland et al. |
| 6,013,448 A | 1/2000 | Braxton et al. |
| 6,013,763 A | 1/2000 | Braisted et al. |
| 6,017,723 A | 1/2000 | Rao et al. |
| 6,057,287 A | 5/2000 | Markland et al. |
| 6,063,764 A | 5/2000 | Creasey et al. |
| 6,071,723 A | 6/2000 | Markland et al. |
| 6,087,473 A | 7/2000 | Conklin et al. |
| 6,090,916 A | 7/2000 | Vlasuk et al. |
| 6,103,499 A | 8/2000 | Markland et al. |
| 6,103,500 A | 8/2000 | Innis et al. |
| 6,113,896 A | 9/2000 | Lazarus et al. |
| 6,126,933 A | 10/2000 | Warne et al. |
| 6,159,938 A | 12/2000 | Gyorkos et al. |
| 6,171,587 B1 | 1/2001 | Wun et al. |
| 6,174,721 B1 | 1/2001 | Innis et al. |
| 6,174,859 B1 | 1/2001 | Lezdey et al. |
| 6,180,607 B1 | 1/2001 | Davies et al. |
| 6,214,966 B1 | 4/2001 | Harris |
| 6,242,414 B1 | 6/2001 | Johnson et al. |
| 6,258,351 B1 | 7/2001 | Harris |
| 6,261,279 B1 | 7/2001 | Demopulos et al. |
| 6,306,884 B1 | 10/2001 | Buckman et al. |
| 6,333,402 B1 | 12/2001 | Markland et al. |
| 6,348,558 B1 | 2/2002 | Harris et al. |
| 6,362,254 B2 | 3/2002 | Harris et al. |
| 6,362,276 B1 | 3/2002 | Harris et al. |
| 6,376,604 B2 | 4/2002 | Kozlowski |
| 6,407,213 B1 | 6/2002 | Carter et al. |
| 6,413,507 B1 | 7/2002 | Bentley et al. |
| 6,423,498 B1 | 7/2002 | Markland et al. |
| 6,432,397 B1 | 8/2002 | Harris |
| 6,455,639 B1 | 9/2002 | Yasukohchi et al. |
| 6,472,195 B2 | 10/2002 | Hillman et al. |
| 6,515,100 B2 | 2/2003 | Harris |
| 6,534,276 B1 | 3/2003 | Wun et al. |
| 6,548,262 B2 | 4/2003 | Gentz et al. |
| 6,576,235 B1 | 6/2003 | Williams et al. |
| 6,583,108 B1 | 6/2003 | Tamburini et al. |
| 6,610,281 B2 | 8/2003 | Harris |
| 6,624,246 B2 | 9/2003 | Kozlowski |
| 6,664,331 B2 | 12/2003 | Harris et al. |
| 6,689,582 B1 | 2/2004 | Davies et al. |
| 6,710,125 B2 | 3/2004 | Kozlowski |
| 6,774,180 B2 | 8/2004 | Kozlowski et al. |
| 6,783,960 B2 | 8/2004 | Innis et al. |
| 6,783,965 B1 | 8/2004 | Sherman et al. |
| 6,806,360 B2 | 10/2004 | Wun et al. |
| 6,814,982 B2 | 11/2004 | Poncin et al. |
| 6,914,135 B2 | 7/2005 | Sheppard et al. |
| 6,953,674 B2 | 10/2005 | Markland et al. |
| 6,989,369 B2 | 1/2006 | Ladner et al. |
| 7,064,107 B2 | 6/2006 | Ladner et al. |
| 7,067,144 B2 | 6/2006 | Demopulos et al. |
| 7,078,383 B2 | 7/2006 | Ley et al. |
| 7,153,829 B2 | 12/2006 | Ladner et al. |
| 7,166,576 B2 | 1/2007 | Cicardi et al. |
| 7,235,530 B2 | 6/2007 | Blair et al. |
| 7,276,480 B1 | 10/2007 | Ladner et al. |
| 7,550,427 B2 | 6/2009 | Ley et al. |
| 7,628,983 B2 | 12/2009 | Markland et al. |
| 7,704,949 B2 | 4/2010 | Ladner et al. |
| 7,718,617 B2 | 5/2010 | Cicardi et al. |
| 7,811,991 B2 | 10/2010 | Ladner et al. |
| 7,851,442 B2 | 12/2010 | Ladner et al. |
| 7,919,462 B2 | 4/2011 | Markland et al. |
| 8,034,775 B2 | 10/2011 | Ladner et al. |
| 8,124,586 B2 | 2/2012 | Ladner et al. |
| 8,188,045 B2 | 5/2012 | Blair et al. |
| 8,283,321 B2 | 10/2012 | Markland et al. |
| 8,710,007 B2 | 4/2014 | Ladner et al. |
| 8,716,225 B2 | 5/2014 | Blair et al. |
| 8,816,055 B2 | 8/2014 | Sexton et al. |
| 8,822,653 B2 | 9/2014 | Sexton et al. |
| 8,828,703 B2 | 9/2014 | Ladner |
| 9,107,928 B2 | 8/2015 | Belichard |
| 9,114,144 B2 | 8/2015 | Ladner et al. |
| 9,266,964 B2 | 2/2016 | Sexton et al. |
| 9,480,733 B2 | 11/2016 | Ladner et al. |
| 9,757,437 B2 | 9/2017 | Blair et al. |
| 10,245,307 B2 | 4/2019 | Ladner et al. |
| 10,336,832 B2 | 7/2019 | Sexton et al. |
| 10,370,453 B2 | 8/2019 | Sexton et al. |
| 10,428,158 B2 | 10/2019 | Conley et al. |
| 2001/0027180 A1 | 10/2001 | Isaacs |
| 2002/0102703 A1 | 8/2002 | Sheppard et al. |
| 2002/0111460 A1 | 8/2002 | Holloway |
| 2003/0012969 A1 | 1/2003 | Clark |
| 2003/0096733 A1 | 5/2003 | Ny et al. |
| 2003/0100070 A1 | 5/2003 | Holloway |
| 2003/0113726 A1 | 6/2003 | Tsuchihashi et al. |
| 2003/0114372 A1 | 6/2003 | White et al. |
| 2003/0138417 A1 | 7/2003 | Kaisheva et al. |
| 2003/0153046 A1 | 8/2003 | Jensen et al. |
| 2003/0175919 A1 | 9/2003 | Ley et al. |
| 2003/0223977 A1 | 12/2003 | Ley et al. |
| 2004/0027782 A1 | 2/2004 | Ladner et al. |
| 2004/0038893 A1 | 2/2004 | Ladner et al. |
| 2004/0044075 A1 | 3/2004 | Staveski et al. |
| 2004/0049018 A1 | 3/2004 | Bailon et al. |
| 2004/0053206 A1 | 3/2004 | Cicardi et al. |
| 2004/0062746 A1 | 4/2004 | Martinez et al. |
| 2004/0062748 A1 | 4/2004 | Martinez et al. |
| 2004/0106747 A1 | 6/2004 | Bailon et al. |
| 2004/0126361 A1 | 7/2004 | Saifer et al. |
| 2004/0152633 A1 | 8/2004 | Jorgensen et al. |
| 2004/0171794 A1 | 9/2004 | Ladner et al. |
| 2004/0180827 A1 | 9/2004 | Chen et al. |

(56) References Cited

U.S. PATENT DOCUMENTS

| | | |
|---|---|---|
| 2004/0209243 A1 | 10/2004 | Nixon et al. |
| 2005/0004021 A1 | 1/2005 | Sprecher et al. |
| 2005/0089515 A1 | 4/2005 | Ley et al. |
| 2005/0164928 A1 | 7/2005 | Ladner et al. |
| 2005/0164945 A1 | 7/2005 | Nixon et al. |
| 2005/0180977 A1 | 8/2005 | Nixon et al. |
| 2005/0222023 A1 | 10/2005 | Hauser |
| 2006/0069020 A1 | 3/2006 | Blair et al. |
| 2006/0194727 A1 | 8/2006 | Ladner et al. |
| 2006/0205671 A1 | 9/2006 | Vinten-Johansen |
| 2006/0228331 A1 | 10/2006 | Peschke et al. |
| 2006/0264603 A1 | 11/2006 | Markland et al. |
| 2007/0020252 A1 | 1/2007 | Ladner et al. |
| 2007/0041959 A1 | 2/2007 | Ley et al. |
| 2007/0049522 A1 | 3/2007 | Ladner et al. |
| 2007/0065407 A1 | 3/2007 | Patten et al. |
| 2007/0075665 A1 | 4/2007 | Claudel et al. |
| 2007/0079096 A1 | 4/2007 | Chen et al. |
| 2007/0100133 A1 | 5/2007 | Beals et al. |
| 2007/0117752 A1 | 5/2007 | Larsen et al. |
| 2007/0213275 A1 | 9/2007 | Clark et al. |
| 2007/0249807 A1 | 10/2007 | Ladner et al. |
| 2007/0253949 A1 | 11/2007 | Golz et al. |
| 2007/0270344 A1 | 11/2007 | Belichard |
| 2008/0038276 A1 | 2/2008 | Sinha et al. |
| 2008/0050716 A1 | 2/2008 | Cicardi et al. |
| 2008/0064637 A1 | 3/2008 | Ladner et al. |
| 2008/0076712 A1 | 3/2008 | Ladner et al. |
| 2008/0131426 A1 | 6/2008 | Ladner et al. |
| 2008/0139473 A1 | 6/2008 | Ladner et al. |
| 2008/0152656 A1 | 6/2008 | Ladner et al. |
| 2008/0182283 A1 | 7/2008 | Markland et al. |
| 2008/0188409 A1 | 8/2008 | Blair et al. |
| 2008/0200646 A1 | 8/2008 | Ladner et al. |
| 2008/0221031 A1 | 9/2008 | Blair et al. |
| 2008/0226655 A1 | 9/2008 | Ladner et al. |
| 2008/0255025 A1 | 10/2008 | Ladner |
| 2008/0260752 A1 | 10/2008 | Ladner et al. |
| 2008/0274969 A1 | 11/2008 | Hauser |
| 2008/0280811 A1 | 11/2008 | Feener |
| 2008/0299050 A1 | 12/2008 | Bortz et al. |
| 2009/0023651 A1 | 1/2009 | Markland et al. |
| 2009/0062195 A1 | 3/2009 | Ladner et al. |
| 2009/0075887 A1 | 3/2009 | Mcpherson |
| 2009/0082267 A1 | 3/2009 | Ladner et al. |
| 2009/0105142 A1 | 4/2009 | Moscicki |
| 2009/0117130 A1 | 5/2009 | Ladner et al. |
| 2009/0123475 A9 | 5/2009 | Siegel |
| 2009/0215119 A1 | 8/2009 | Ladner |
| 2009/0221480 A1 | 9/2009 | Blair et al. |
| 2009/0227494 A1 | 9/2009 | Blair et al. |
| 2009/0227495 A1 | 9/2009 | Blair et al. |
| 2009/0233852 A1 | 9/2009 | Blair et al. |
| 2009/0234009 A1 | 9/2009 | Blair et al. |
| 2009/0247452 A1 | 10/2009 | Ellis et al. |
| 2009/0247453 A1 | 10/2009 | Blair et al. |
| 2009/0264350 A1 | 10/2009 | Blair et al. |
| 2010/0034805 A1 | 2/2010 | Ladner et al. |
| 2010/0183625 A1 | 7/2010 | Sternlicht |
| 2010/0273721 A1 | 10/2010 | Belichard |
| 2010/0285507 A1 | 11/2010 | Cho et al. |
| 2010/0286061 A1 | 11/2010 | Devy et al. |
| 2011/0008762 A1 | 1/2011 | Cicardi et al. |
| 2011/0086801 A1 | 4/2011 | Ladner |
| 2011/0136746 A1 | 6/2011 | Markland et al. |
| 2011/0172140 A1 | 7/2011 | Ley et al. |
| 2011/0200611 A1 | 8/2011 | Sexton |
| 2012/0015811 A1 | 1/2012 | Ladner et al. |
| 2012/0201756 A1 | 8/2012 | Sexton |
| 2012/0264798 A1 | 10/2012 | Sinha et al. |
| 2012/0322744 A1 | 12/2012 | Ley et al. |
| 2012/0328517 A1 | 12/2012 | Markland et al. |
| 2013/0012438 A1 | 1/2013 | Blair et al. |
| 2014/0288001 A1 | 9/2014 | Blair et al. |
| 2014/0303357 A1 | 10/2014 | Lim et al. |
| 2014/0335023 A1 | 11/2014 | Sexton et al. |
| 2014/0349940 A1 | 11/2014 | Ladner et al. |
| 2015/0274841 A1 | 10/2015 | Conley et al. |
| 2015/0362492 A1 | 12/2015 | Joseph et al. |
| 2015/0368359 A1 | 12/2015 | Belichard |
| 2016/0017055 A1 | 1/2016 | Nixon et al. |
| 2016/0102150 A1 | 4/2016 | Sexton et al. |
| 2016/0361395 A1 | 12/2016 | Ladner et al. |
| 2017/0002094 A1 | 1/2017 | Sexton et al. |
| 2018/0002447 A1 | 1/2018 | Sexton et al. |
| 2018/0002448 A1 | 1/2018 | Sexton et al. |
| 2018/0002449 A1 | 1/2018 | Sexton et al. |
| 2018/0037664 A1 | 2/2018 | Sexton et al. |
| 2018/0037665 A1 | 2/2018 | Sexton et al. |
| 2018/0037666 A1 | 2/2018 | Sexton et al. |
| 2018/0298110 A1 | 10/2018 | Chyung et al. |
| 2018/0362664 A1 | 12/2018 | Adelman et al. |
| 2019/0185580 A1 | 6/2019 | Nixon et al. |
| 2020/0017602 A1 | 1/2020 | Sexton et al. |
| 2020/0109213 A1 | 4/2020 | Sexton et al. |
| 2020/0109214 A1 | 4/2020 | Peng et al. |
| 2020/0317815 A1 | 10/2020 | Mendivil Medina et al. |

FOREIGN PATENT DOCUMENTS

| | | |
|---|---|---|
| CN | 101928346 A | 12/2010 |
| CN | 103635489 A | 3/2014 |
| EP | 1 736 465 A1 | 12/2006 |
| JP | 09-509048 | 9/1997 |
| JP | 09-509838 | 10/1997 |
| JP | H9-509838 | 10/1997 |
| JP | 09-511131 | 11/1997 |
| JP | 10-503375 | 3/1998 |
| JP | 10-510996 | 10/1998 |
| JP | 2009-529553 A | 8/2009 |
| JP | 2013-516478 A | 5/2013 |
| WO | WO 87/05396 A1 | 9/1987 |
| WO | WO 1995/21601 | 8/1995 |
| WO | WO 1999/21558 | 5/1999 |
| WO | WO 2002/20569 | 3/2002 |
| WO | WO 2002/30393 | 4/2002 |
| WO | WO 2003/066824 | 8/2003 |
| WO | WO 2003/103475 | 12/2003 |
| WO | WO 2004/019968 | 3/2004 |
| WO | WO 2005/021556 | 3/2005 |
| WO | WO 2005/021557 | 3/2005 |
| WO | WO 2005/095327 A1 | 10/2005 |
| WO | WO 2006/036860 | 4/2006 |
| WO | WO 2006/091459 | 8/2006 |
| WO | WO 2007/104541 A2 | 9/2007 |
| WO | WO 2007/106746 | 9/2007 |
| WO | WO 2008/016883 A2 | 2/2008 |
| WO | WO 2009/026334 | 2/2009 |
| WO | WO 2009/026539 | 2/2009 |
| WO | WO 2010/048432 | 4/2010 |
| WO | WO 2010/080833 A1 | 7/2010 |
| WO | WO 2011/085103 | 7/2011 |
| WO | WO 2012/094587 | 7/2012 |
| WO | WO 2014/113701 A1 | 7/2014 |
| WO | WO 2014/113712 A1 | 7/2014 |
| WO | WO 2014/152232 A2 | 9/2014 |
| WO | WO 2015/112578 A1 | 7/2015 |
| WO | WO 2015/148790 A1 | 10/2015 |
| WO | WO 2016/160926 A1 | 10/2016 |
| WO | WO 2017/100679 A1 | 6/2017 |

OTHER PUBLICATIONS

[No Author Listed], Central and Branch Retinal Artery Occlusion—Merck Manual, 1-3 pp. accessed Sep. 26, 2013.

[No Author Listed], Diabetic Retinopathy—Merck Manual, 1-3 pp. accessed Sep. 26, 2013.

[No Author Listed], Hypertensive Retinopathy—Merck manual, pp. 1-2, accessed Sep. 26, 2013.

[No Author Listed], Retinal Vascular Disease. Retrieved from http://dro.hs.columbia.edu/vr3.htm, 1-2 pp. accessed Sep. 26, 2013.

[No Author Listed], Retinopathy of Prematurity—Merck manual, 1-2 pp., accessed Sep. 26, 2013.

(56) References Cited

OTHER PUBLICATIONS

Abdouh et al., Early upregulation of kinin B1 receptors in retinal microvessels of the streptozotocin-diabetic rat. Br J Pharmacol. Sep. 2003;140(1):33-40.
Bagdasarian et al., Immunochemical studies of plasma kallikrein. J Clin Invest. Dec. 1974;54(6):1444-54.
Barnard, Retinal Vascular Disorders. Retrieved from http://www.academy.org.uk/lectures/barnard5.htm. 1-4 pp., accessed Sep. 26, 2013.
Beck et al., Combination of Aminocaproic Acid and Nicardipine in Treatment of Aneurysmal Subarachnoid Hemorrhage. Stroke. 1988;19(1):63-67.
Bendig, Humanization of Rodent Monoclonal Antibodies by CDR Grafting. Companion to Methods in Enzymology. 1995;8:83-93.
Boyd et al., Correlation of increased vascular endothelial growth factor with neovascularization and permeability in ischemic central vein occlusion. Arch Ophthalmol. Dec. 2002;120(12):1644-50.
Breedveld, Therapeutic monoclonal antibodies. Lancet. Feb. 26, 2000;355(9205):735-40. Review.
Casset et al., A peptide mimetic of an anti-CD4 monoclonal antibody by rational design. Biochem Biophys Res Commun. Jul. 18, 2003;307(1):198-205.
Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.
Ciulla et al., Diabetic retinopathy and diabetic macular edema: pathophysiology, screening, and novel therapies. Diabetes Care. Sep. 2003;26(9):2653-64.
Dai et al., Role of plasma kallikrein-kinin system activation in synovial recruitment of endothelial progenitor cells in experimental arthritis. Arthritis Rheum. Nov. 2012;64(11):3574-82. doi: 10.1002/art.34607.
Delaria et al., Characterization of placental bikunin, a novel human serine protease inhibitor. J Biol Chem. May 2, 1997;272(18):12209-14.
Dennis et al., Potent and selective Kunitz domain inhibitors of plasma kallikrein designed by phage display. J Biol Chem. Oct. 27, 1995;270(43):25411-7.
Devani et al., Kallikrein-kinin system in inflammatory bowel diseases: Intestinal involvement and correlation with the degree of tissue inflammation. Dig Liver Dis. Sep. 2005;37(9):665-73.
Dotsenko et al., Hageman factor and kallikrein in pathogenesis of senile cataracts and the pseudoexfoliation syndrome. Immunopharmacology. May 1996;32(1-3):141-5.
Fareed, A Review of Diabetic Macular Edema. DJO Digital Journal of Ophthalmology. Jul. 1, 1997;3(6):1-7.
Feener, Plasma kallikrein and diabetic macular edema. Curr Diab Rep. Aug. 2010;10(4):270-5. doi: 10.1007/s11892-010-0127-1.
Ferrara et al., Recombinant renewable polyclonal antibodies. MAbs. 2015;7(1):32-41. doi: 10.4161/19420862.2015.989047.
Fink et al., Cellular expression of plasma prekallikrein in human tissues. Biol Chem. Sep. 2007;388(9):957-63.
Frank, 8. Hereditary angioedema. J Allergy Clin Immunol. Feb. 2008;121(2 Suppl):S398-401; quiz S419. doi: 10.1016/j.jaci.2007.07.057.
Frumento et al., Stroke after cardiac surgery: a retrospective analysis of the effect of aprotinin dosing regimens. Ann Thorac Surg. Feb. 2003;75(2):479-83; discussion 483-4.
Gallimore et al., Studies on plasma inhibitors of plasma kallikrein using chromogenic peptide substrate assays. Thromb Res. 1979;16(5-6):695-703.
Gao et al., Extracellular carbonic anhydrase mediates hemorrhagic retinal and cerebral vascular permeability through prekallikrein activation. Nat Med. Feb. 2007;13(2):181-8. Epub Jan. 28, 2007.
Gao et al., Kallikrein-binding protein inhibits retinal neovascularization and decreases vascular leakage. Diabetologia. May 2003;46(5):689-98. Epub May 13, 2003.
Gillies, Regulators of vascular permeability: potential sites for intervention in the treatment of macular edema. Doc Ophthalmol. 1999;97(3-4):251-60.

Green, Antibody engineering via genetic engineering of the mouse: XenoMouse strains are a vehicle for the facile generation of therapeutic human monoclonal antibodies. J Immunol Methods. Dec. 10, 1999;231(1-2):11-23.
Han Lee et al., Approaches toward reversal of increased vascular permeability in C1 inhibitor deficient mice. Immunol Lett. Oct. 31, 2003;89(2-3):155-60.
Hatcher et al., Kallikrein-binding protein levels are reduced in the retinas of streptozotocin-induced diabetic rats. Invest Ophthalmol Vis Sci. Mar. 1997;38(3):658-64.
Kedzierska et al., Plasma prekallikrein as a risk factor for diabetic retinopathy. Arch Med Res. Sep.-Oct. 2005;36(5):539-43.
Kenniston et al., Discovery and Characterization Of a Highly Specific Antibody Inhibitor Of Plasma Kallikrein. Blood 2013;122:1067. Abstract only.
Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.
Kettleborough et al., Humanization of a mouse monoclonal antibody by CDR-grafting: the importance of framework residues on loop conformation. Protein Eng. Oct. 1991;4(7):773-83.
Kondo et al., A simple and sensitive method for determination of human urinary kallikrein activity (kininogenase activity), using human low molecular weight kininogen. Endocrinol Jpn. Oct. 1984;31(5):635-43.
Lawson et al., Enhanced dermal and retinal vascular permeability in streptozotocin-induced type 1 diabetes in Wistar rats: blockade with a selective bradykinin B1 receptor antagonist. Regul Pept. Jan. 15, 2005;124(1-3):221-4.
Lederman et al., A Single Amino Acid Substitution in a Common African Allele of the CD4 Molecule Ablates Binding of the Monoclonal Antibody, OKT4. Molecular Immunology. 1991;28(11):1171-1181.
Levy et al., The therapeutic potential of a kallikrein inhibitor for treating hereditary angioedema. Expert Opin Investig Drugs. Sep. 2006;15(9):1077-90.
Ley et al., Obtaining a family of high-affinity, high-specificity protein inhibitors of plasmin and plasma kallikrein. Mol Divers. Oct. 1996;2(1-2):119-24.
Li et al., β-Endorphin omission analogs: Dissociation of immunoreactivity from other biological activities. Proc. Natl. Acad. Sci. USA. Jun. 1980;77(6):3211-3214.
Liu et al., Plasma kallikrein-kinin system and diabetic retinopathy. Biol Chem. Mar. 2013;394(3):319-28. doi: 10.1515/hsz-2012-0316. Author manuscript.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.
Ma et al., Expression and cellular localization of the kallikrein-kinin system in human ocular tissues. Exp Eye Res. Jul. 1996;63(1):19-26.
Ma et al., Kallistatin in human ocular tissues: reduced levels in vitreous fluids from patients with diabetic retinopathy. Curr Eye Res. Nov. 1996;15(11):1117-23.
Ma et al., Treatment of retinal edema using peptide angiogenic inhibitors. Biosis. 2003.
MacCallum et al., Antibody-antigen interactions: contact analysis and binding site topography. J Mol Biol. Oct. 11, 1996;262(5):732-45.
Mahdy et al., Perioperative systemic haemostatic agents. Br J Anaesth. Dec. 2004;93(6):842-58. Epub Jul. 26, 2004.
Markland et al., Iterative optimization of high-affinity protease inhibitors using phage display. 2. Plasma kallikrein and thrombin. Biochemistry. Jun. 18, 1996;35(24):8058-67.
Marlor et al., Identification and cloning of human placental bikunin, a novel serine protease inhibitor containing two Kunitz domains. J Biol Chem. May 2, 1997;272(18):12202-8.
Nambu et al., Angiopoietin 1 inhibits ocular neovascularization and breakdown of the blood-retinal barrier. Gene Ther. May 2004;11(10):865-73.

(56) References Cited

OTHER PUBLICATIONS

Okano et al., Chapter 9.1.2 Drug Action and Blood Concentration. Shin Yakuzaiaku Soron, revised 3rd Edition, Apr. 10, 1987:250-253.
Paul, Fv Structure and Diversity in Three Dimensions. Fundamental Immunology, 3rd Edition. 1993: 292-5.
Phipps et al., Plasma kallikrein mediates angiotensin II type 1 receptor-stimulated retinal vascular permeability. Hypertension. Feb. 2009;53(2):175-81. doi:10.1161/HYPERTENSIONAHA.108.117663. Epub Jan. 5, 2009. With 5 page Online Supplement.
Pinna et al., Levels of human tissue kallikrein in the vitreous fluid of patients with severe proliferative diabetic retinopathy. Ophthalmologica. Jul.-Aug. 2004;218(4):260-3.
Ritchie, Protease inhibitors in the treatment of hereditary angioedema. Transfus Apher Sci. Dec. 2003;29(3):259-67. Abstract only.
Roos et al., Antifibrinolytic therapy for aneurysmal subarachnoid haemorrhage. Cochrane Database Syst Rev. 2003;(2):CD001245. Review. Update in: Cochrane Database Syst Rev. 2013;8:CD001245.
Schneider et al., Critical role of kallikrein in hereditary angioedema pathogenesis: a clinical trial of ecallantide, a novel kallikrein inhibitor. J Allergy Clin Immunol. Aug. 2007;120(2):416-22. Epub Jun. 7, 2007.
Sexton et al., Comparison Of Plasma Kallikrein Inhibition By The Endogenous C1-Inhibitor Versus DX-2930, a Monoclonal Antibody Inhibitor. Blood. 2013;122:1066. Abstract only.
Sexton et al., Discovery and characterization of fully human monoclonal antibody inhibitor of plasma kallikrein for the treatment of plasma kallikrein-mediated edema. J Allergy Clin Immunol. Feb. 2013;131(2):AB32. Suppl S. Annual meeting of the American Academy of Allergy, Asthma, and Immunology. San Antonio, TX, USA; Feb. 22-26.
Sexton et al., Specific inhibition of tissue kallikrein 1 with a human monoclonal antibody reveals a potential role in airway diseases. Biochem J. Aug. 13, 2009;422(2):383-92. doi: 10.1042/BJ20090010.
Shariat-Madar et al., Assembly and activation of the plasma kallikrein/kinin system: a new interpretation. Int Immunopharmacol. Dec. 2002;2(13-14):1841-9.
Sonoda et al., [Ophthalmological (retinal) pathology and inflammation.] Kekkann Igaku. Oct. 2003;4(5):61-6.
Tanaka et al., Evaluation of a novel kallikrein inhibitor on hemostatic activation in vitro. Thromb Res. 2004;113(5):333-9.
Tang et al., Expression, crystallization, and three-dimensional structure of the catalytic domain of human plasma kallikrein. J Biol Chem. Dec. 9, 2005;280(49):41077-89. Epub Sep. 30, 2005.
Veloso et al., A monoclonal anti-human plasma prekallikrein antibody that inhibits activation of prekallikrein by factor XIIa on a surface. Blood. Oct. 1987;70(4):1053-62.
Veronez et al., The involvement of proteoglycans in the human plasma prekallikrein interaction with the cell surface. PLoS One. Mar. 12, 2014;9(3):e91280. doi: 10.1371/journal.pone.0091280. eCollection 2014.
Wark, DX-890 (Dyax). IDrugs. Jun. 2002;5(6):586-9.
Weaver, Animal studies paint misleading picture. Nature International Weekly Journal of Science. Published online Mar. 30, 2010. Retrieved on Aug. 1, 2017 from http://www.nature.com/news.2010.158.html.
Williams et al., DX-88 and HAE: a developmental perspective. Transfus Apher Sci. Dec. 2003; 29(3):255-8.
Yayama et al., Tissue kallikrein is synthesized and secreted by human vascular endothelial cells. Biochim Biophys Acta. Feb. 17, 2003;1593(2-3):231-8.
[No Author Listed] Efficacy and Safety Study of DX-2930 to prevent acute angioedema attacks in patients with Type I and Type II HAE. Study NCT02586805. ClinicalTrials.gov Apr. 9, 2019. 7pgs.
Banerji et al., Effect of Lanadelumab Compared With Placebo on Prevention of Hereditary Angioedema Attacks: A Randomized Clinical Trial. JAMA. Nov. 27, 2018;320(20):2108-2121. doi: 10.1001/jama.2018.16773.
Banerji et al., Inhibiting Plasma Kallikrein for Hereditary Angioedema Prophylaxis. N Engl J Med. Feb. 23, 2017;376(8):717-728. doi: 10.1056/NEJMoa1605767.
Banerji et al., Lanadelumab 300mg every 2 weeks effectively prevented hereditary angioedema attacks in the help study. Ann Allerg Asthma Im. Nov. 1, 2018;121(5):S5.
Bova et al., Lanadelumab Injection Treatment For The Prevention Of Hereditary Angioedema (HAE): Design, Development And Place In Therapy. Drug Des Devel Ther. Oct. 22, 2019; 13:3635-3646. doi: 10.2147/DDDT.S192475.
Busse et al., Efficacy and safety of lanadelumab for prophylactic treatment in adolescents with hereditary angioedema (HAE). Feb. 2019;143(2): AB43.
Lumry et al., Subcutaneous self-administration of lanadelumab for prophylactic treatment in patients with hereditary angioededma (HAE). Ann Allerg Asthma Im. Nov. 2018;121(5): S57.
Riedl et al., An open-label study to evaluate the long-term safety and efficacy of lanadelumab for prevention of attacks in hereditary angioedema: design of the HELP study extension. Clin Transl Allergy. Oct. 6, 2017; 7: 36. doi: 10.1186/s13601-017-0172-9.
Wedi, Lanadelumab to treat hereditary angioedema. Drugs Today (Barc). Jul. 2019;55(7):439-448. doi: 10.1358/dot.2019.55.7.2985293.
Wedner et al., Modeling and Analyses to Identify Potential Dosing Regimens of DX-2930 for the Long-Term Prophylaxis of Hereditary Angioedema. J All Clin Immunol. Feb. 1, 2016;137(2):AB252.
Wu, Lanadelumab for the treatment of hereditary angioedema. Expert Opin Biol Ther. Dec. 2019;19(12):1233-1245. doi: 10.1080/14712598.2019.1685490. Epub Nov. 4, 2019.
Zuraw, HAE therapies: past present and future. Allergy Asthma Clin Immunol. Jul. 28, 2010;6(1):23. doi: 10.1186/1710-1492-6-23.
U.S. Appl. No. 16/199,453, filed Nov. 26, 2018, Nixon et al.
U.S. Appl. No. 16/445,304, filed Jun. 19, 2019, Sexton et al.
U.S. Appl. No. 16/411,242, filed May 14, 2019, Sexton et al.
U.S. Appl. No. 15/113,297, filed Jul. 21, 2016, Sexton et al.
U.S. Appl. No. 15/562,671, filed Sep. 28, 2017, Chyung et al.
U.S. Appl. No. 16/061,103, filed Jun. 7, 2018, Adelman et al.
EP 15740774.3, Jul. 24, 2017, Extended European Search Report.
EP 15769534.7, Aug. 11, 2017, Extended European Search Report.
PCT/US2015/022715, Jul. 2, 2015, International Search Report and Written Opinion.
PCT/US2015/022715, Oct. 6, 2016, International Preliminary Report on Patentability.
U.S. Appl. No. 17/010,354, filed Sep. 2, 2020, Sexton et al.

Figure 3

Light V gene = VK1_L12 HK102/v1/L12a;   J gene = JK1

```
                         FR1                         CDR1                    FR2                      CDR2
559A-M0162-A04:  DIQMTQSPSTLSASVGDRVTITC  RASQSISSWLA  WYQQKPGKAPXLLIY  KASTLES
                 DIQMTQSPSTLSASVGDRVTITC  RASQSISSWLA  WYQQKPGKAP LLIY  AS+LES
Germline:        DIQMTQSPSTLSASVGDRVTITC  RASQSISSWLA  WYQQKPGKAPXLLIY  DASSLES FR3                              CDR3             FR4
559A-M0162-A04:  GVPSRFSGSGSGTEFTLTISSLQPDDFATYYC  QQYNTYWT  FGQGTKVEIK
                 GVPSRFSGSGSGTEFTLTISSLQPDDFATYYC  QQYN+YWT  FGQGTKVEIK
Germline:        GVPSRFSGSGSGTEFTLTISSLQPDDFATYYC  QQYNSYWT  FGQGTKVEIK
```

Heavy V gene = VH3_3-23;   J gene = JH3

```
                         FR1                                CDR1           FR2                     CDR2
559A-M0162-A04:  EVQLLESGGGLVQPGGSLRLSCAASGFTFS  HYIMM  WVRQAPGKGLEWVS  GIYSSGGITVYADSVKG
                 EVQLLESGGGLVQPGGSLRLSCAASGFTFS  Y M    WVRQAPGKGLEWVS  I  SGG T YADSVKG
Germline:        EVQLLESGGGLVQPGGSLRLSCAASGFTFS  SYAMS  WVRQAPGKGLEWVS  AISGSGGSTYYADSVKG FR3                               CDR3                    FR4
559A-M0162-A04:  RFTISRDNSKNTLYLQMNSLRAEDTAVYYCAX  RRTGIPRRDAFDI  WGQGTMVTVSS
                 RFTISRDNSKNTLYLQMNSLRAEDTAVYYCA             AFDI  WGQGTMVTVSS
Germline:        RFTISRDNSKNTLYLQMNSLRAEDTAVYYCAK            AFDI  WGQGTMVTVSS
```

Figure 4

```
391
 |  IVGGTNSSWG EWPWQVSLQV KLTAQRHLCG GSLIGHQWVL TAAHCFDGLP
441                                                     490
 |  LQDVWRIYSG ILNLSDITKD TPFSQIKEII IHQNYKVSEG NHDIALIKLQ
491                                                     540
 |  APLNYTEFQK PICLPSKGDT STIYTNCWVT GWGFSKEKGE IQNILQKVNI
541                                                     590
 |  PLVTNEECQK RYQDYKITQR MVCAGYKEGG KDACKGDSGG PLVCKHNGMW
591                                                     638
 |  RLVGITSWGE GCARREQPGV YTKVAEYMDW ILEKTQSSDG KAQMQSPA
```

440

Figure 5A
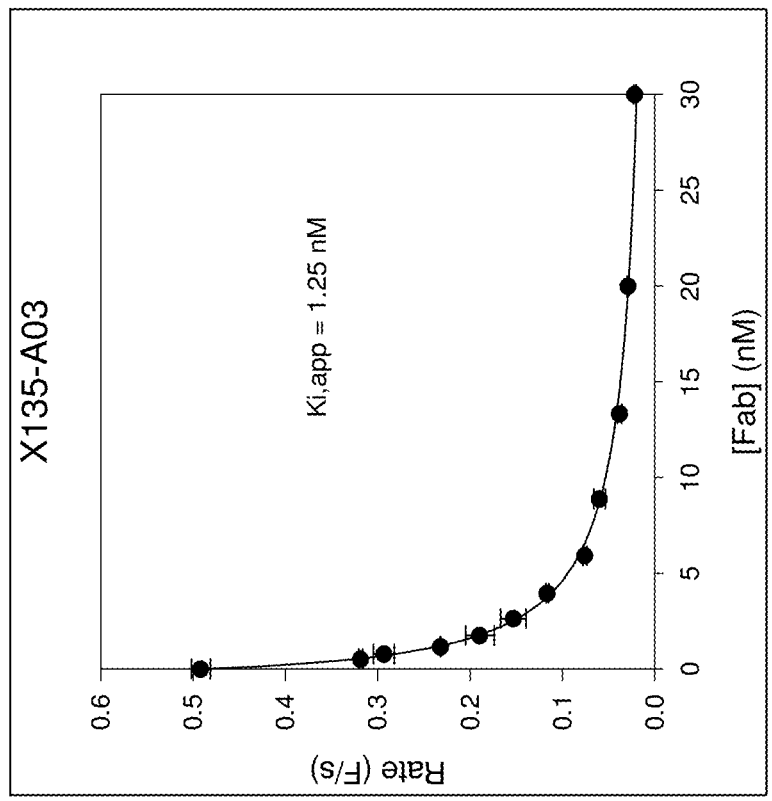
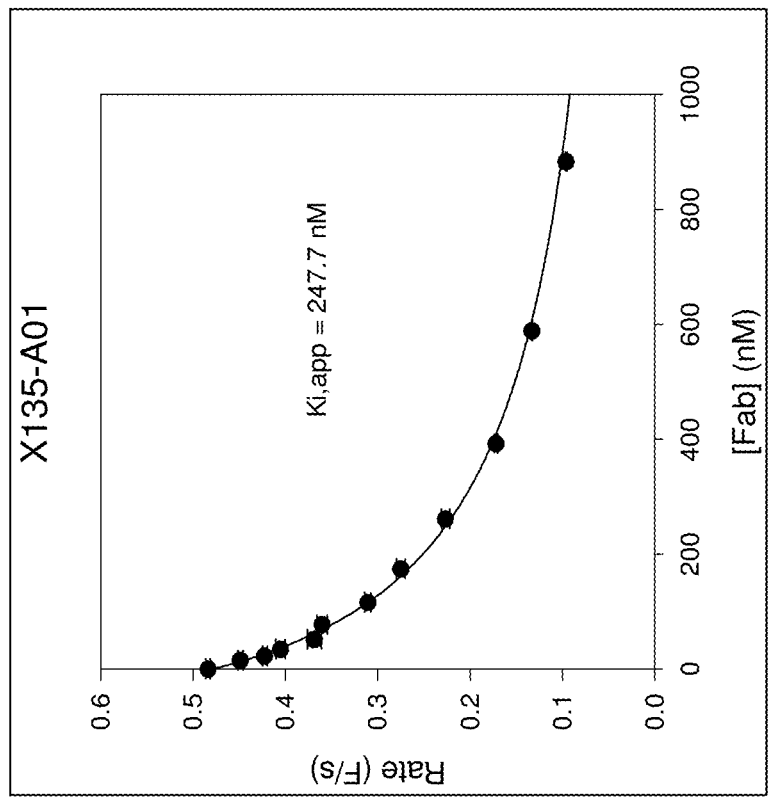

Figure 7A

```
                  391
                    |
(klkb1)-Mut1-forPichia    IVGGTNSSWG EWPWQVSLQV KLTAQRHLCG GSLIGHQWVL TAAHCFDGLP
(klkb1)-Mut2-forPichia    IVGGTNSSWG EWPWQVSLQV KLTAQRHLCG GSLIGHQWVL TAAHCFDGLP
(klkb1)-Mut3-forPichia    IVGGTNSSWG EWPWQVSLQV KLTAQRHLCG GSLIGHQWVL TAAHCFDGLP
(klkb1)-Mut4-forPichia    IVGGTASAAG EWPWQVSLQV KLTAQRHLCG GSLIGHQWVL TAAHCFDGLP
(klkb1)-parentforPichia   IVGGTNSSWG EWPWQVSLQV KLTAQRHLCG GSLIGHQWVL TAAHCFDGLP 441                                                        490
                    |                                                          |
(klkb1)-Mut1-forPichia    LQDVWRIYSG ILNLSDITKD TPFSQIKEII IHQNYKVAEG AHDIALIKLQ
(klkb1)-Mut2-forPichia    LQDVWRIYSG ILNLSDITKD TPFSQIKEII IHQNYKVSEG NHDIALIKLQ
(klkb1)-Mut3-forPichia    LQDVWRIYSG ILNLSDITKD TPFSQIKEII IHQNYKVSEG NHDIALIKLQ
(klkb1)-Mut4-forPichia    LQDVWRIYSG ILNLSDITKD TPFSQIKEII IHQNYKVSEG NHDIALIKLQ
(klkb1)-parentforPichia   LQDVWRIYSG ILNLSDITKD TPFSQIKEII IHQNYKVSEG NHDIALIKLQ 491                                                        540
                    |                                                          |
(klkb1)-Mut1-forPichia    APLNYTEFQK PISLPAAGDT STIYTNCWVT GWGFSKEKGE IQNILQKVNI
(klkb1)-Mut2-forPichia    APLNYTEFQK PISLPSKGDT STIYTNCWVT GWGFSKEKGE IQNILQKVNI
(klkb1)-Mut3-forPichia    APLNYTEFQK PISLPSKGDT STIYTNCWVT GWGFSKEKGE IQNILQKVNI
(klkb1)-Mut4-forPichia    APLNYTEFQK PISLPSKGDT STIYTNCWVT GWGFSKEKGE IQNILQKVNI
(klkb1)-parentforPichia   APLNYTEFQK PISLPSKGDT STIYTNCWVT GWGFSKEKGE IQNILQKVNI 541                                                        590
                    |                                                          |
(klkb1)-Mut1-forPichia    PLVTNEECQK RYQDYKITQR MVCAGYKEGG KDACKGDSGG PLVCKHNGMW
(klkb1)-Mut2-forPichia    PLVTNEECQK AYADAKIAQA MVCAGYKEGG KDACKGDSGG PLVCKHNGMW
(klkb1)-Mut3-forPichia    PLVTNEECQK RYQDYKITQR MVCAGYKEGG KAACAGASGG PLVCKHNGMW
(klkb1)-Mut4-forPichia    PLVTNEECQK RYQDYKITQR MVCAGYKEGG KDACKGDSGG PLVCKHNGMW
(klkb1)-parentforPichia   PLVTNEECQK RYQDYKITQR MVCAGYKEGG KDACKGDSGG PLVCKHNGMW
```

Figure 7B

```
                         591                                                                                    638
                          |                                                                                      |
(klkb1)-Mut1-forPichia    RLVGITSWGE GCARREQPGV YTKVAEYMDW ILEKTQSSDG KAQMQSPA
(klkb1)-Mut2-forPichia    RLVGITSWGE GCARREQPGV YTKVAEYMDW ILEKTQSSDG KAQMQSPA
(klkb1)-Mut3-forPichia    RLVGITSWGE GCARREQPGV YTKVAEYMDW ILEKTQSSDG KAQMQSPA
(klkb1)-Mut4-forPichia    RLVGITSWGE GCARREQPGV YTKVAEYMDW ILEKTQSSDG KAQMQSPA
(klkb1)-parentforPichia   RLVGITSWGE GCARREQPGV YTKVAEYMDW ILEKTQSSDG KAQMQSPA
```

COMPOSITIONS AND METHODS FOR TREATMENT OF DIABETIC MACULAR EDEMA

CROSS-REFERENCE TO RELATED APPLICATIONS

This application is a continuation of U.S. application Ser. No. 14/669,607, filed Mar. 26, 2015, which claims the benefit under 35 U.S.C. § 119(e) of U.S. provisional application Ser. No. 61/971,170, filed Mar. 27, 2014, each of which is herein incorporated by reference in its entirety.

BACKGROUND OF THE INVENTION

Retinal diseases affect the area of the retina that serves the central vision. While many retinal diseases share common symptoms, each has unique characteristics.

Diabetic macular edema (DME) is a swelling of the macula caused by retinal blood vessel leakage that occurs in patients with diabetes. DME is the major cause of vision loss in people with diabetic retinopathy. People with diabetes have a 10 percent risk of developing the DME during their lifetime. DME affects up to 30% of people who have had diabetes for more than 20 years. If left untreated, DME can result in moderate to severe vision loss.

SUMMARY OF THE INVENTION

The present disclosure is based, in part, on studies showing that animal models of diabetic macular edema and retinal diseases can be treated with DX-2944, a Fab antibody that binds to active PKal.

Some aspects of the disclosure relate to a method for treating a retinal disease, such as diabetic macular edema (DME), age-related macular degeneration, retinal vein occlusion, uveitis, endophthalmitis, polypoidal choroidal vasculopathy (PCV), or any other retinal disease presenting with macular edema, in a subject, the method comprising administering (e.g., via intravitreal injection, intraocular injection, or subcutaneous injection) an effective amount of a composition comprising an antibody that specifically binds to active plasma kallikrein (PKal) to a subject in need thereof.

In some embodiments, the antibody does not bind to human prekallikrein. In some embodiments, the antibody specifically binds to a catalytic domain of human PKal. In some embodiments, the antibody interacts with one or more amino acid residues in the active human PKal and inhibits its activity by at least 50%. The one or more amino acid residues may be one or more of V410, L412, T413, A414, Q415, R416, L418, C419, H434, C435, F436, D437, G438, L439, W445, Y475, K476, V477, S478, E479, G480, D483, F524, E527, K528, Y552, D554, Y555, A564, D572, A573, C574, K575, G576, S578, T596, S597, W598, G599, E600, G601, C602, A603, R604, Q607, P608, G609, V610, and Y611. In some embodiments, the antibody binds an epitope that comprises the segment of V410-C419, H434-L439, Y475-G480, F524-K528, Y552-Y555, D572-S578, T596-R604, or Q607-Y611.

In some embodiments, the antibody inhibits the activity of the active PKal by at least 80%. In some embodiments, the antibody has an apparent Ki ($K_{i,app}$) lower than about 1 nM. In some embodiments, the antibody has a $K_{i,app}$ lower than about 0.1 nM. In some embodiments, the antibody has a $K_{i,app}$ lower than about 0.05 nM. In some embodiments, the antibody has a binding affinity ($K_D$) for the active PKal of less than $10^{-6}$M. In some embodiments, the antibody preferentially binds the active PKal as relative to a mutant of the active PKal that contains one or more mutations at positions R551, Q553, Y555, T558, and R560.

In some embodiments, the antibody comprises a heavy chain variable region that comprises complementarity determining region 1 (HC CDR1), complementarity determining region 2 (HC CDR2), and complementarity determining region 3 (HC CDR3), and wherein the HC CDR3 comprises the motif $X_{99}R_{100}X_{101}G_{102}X_{103}P_{104}R_{105}X_{106}X_{107}X_{108}X_{109}X_{110}X_{111}$, in which: $X_{99}$ is R or Q; $X_{101}$ is T, I, R, S, or P; $X_{103}$ is V, I, or L; $X_{106}$ is R or W; $X_{107}$ is D or N; $X_{108}$ is A, S, D, E, or V; $X_{109}$ is F or L; $X_{110}$ is D, E, or N, and $X_{111}$ is I, N, M, or S (SEQ ID NO:15). In some embodiments, $X_{99}$ is Q and $X_{101}$ is I, R, S, or P. In some embodiments, $X_{106}$ is W and $X_{111}$ is N, M, or S. In some embodiments, $X_{101}$ is I, $X_{108}$ is E, and $X_{103}$ is I or L. In some embodiments, $X_{101}$ is I and $X_{103}$ is I or L. In some embodiments, $X_{103}$ is I or L and $X_{110}$ is D, E, or N. In some embodiments, the heavy chain variable region includes $H_{31}$ in the HC CDR1. In some embodiments, the heavy chain variable region includes $F_{27}$, $F_{29}$, or both in the framework region 1 (FR1).

In some embodiments, the antibody further comprises a light chain variable region that comprises complementarity determining region 1 (LC CDR1), complementarity determining region 2 (LC CDR2), and complementarity determining region 3 (LC CDR3). In some embodiments, the LC CDR2 includes $K_{50}$, $L_{54}$, $E_{55}$, $S_{56}$, or a combination thereof. In some embodiments, the light chain variable region further includes $G5_7$ in the framework region 3 (FR3). In some embodiments, the light chain variable includes $N_{45}$ or $K_{45}$ in the framework region 2 (FR2).

In some embodiments, the antibody binds to the same epitope as DX-2944 or competes for binding to the active PKal with DX-2944. Such an antibody may comprise a heavy chain (HC) CDR1, HC CDR2, and HC CDR3 of DX-2930 and a light chain (LC) CDR1, LC CDR2, and LC CDR3 of DX-2930. In some embodiments, the antibody comprises the HC variable domain of DX-2930 (SEQ ID NO:3) and the LC variable domain of DX-2930 (SEQ ID NO:4). In one example, the antibody is DX-2944.

In any of the methods described herein, the antibody can be a full-length antibody or an antigen-binding fragment thereof. In some embodiments, the antibody is a Fab. In some embodiments, the antibody is a human antibody or a humanized antibody.

Also within the scope of the present disclosure are (i) pharmaceutical compositions for use in treating a retinal disease (e.g., DME, AMD, RVO, uveitis, endophthalmitis, or PCV), the compositions comprising one or more antibodies binding to active PKal (e.g., those described herein) and a pharmaceutically acceptable carrier, and (ii) uses of such compositions or antibodies for manufacturing a medicament for use in treating the retinal disease.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 3 shows the amino acid sequence of the heavy chain variable region (VH) and light chain variable region (VL) of a parent antibody, M0162-A04, from which DX2930 was derived, and their alignment with the corresponding germline VH and VL genes as indicated. Variations in M0162-A04 as compared to the germline sequences are indicated (boldfaced). The sequences in FIG. 3, from top to bottom, correspond to SEQ ID NOS: 16-18 (light V gene) and SEQ ID NOS: 19-21.

FIG. 4 shows the amino acid sequence of the catalytic domain of human plasma kallikrein (residues 391-638 of the full length human PKal) (SEQ ID NO:22). The boldfaced and underlined residues refer to those that are involved in the interaction with the Fab fragment of DX2930 as identified by the crystal structure discussed in Example 2 below.

FIGS. 5A-5D are a series of graphs showing the apparent kI ($K_{i,app}$) of a number of antibody mutants derived from M0162-A04 against human Pkal, including: X135-A01 and X135-A03 (FIG. 5A), M162-A04 and X133-B02 (FIG. 5B), X133-D06 and X133-F10 (FIG. 5C), and X133-G05 and M199-A08 (FIG. 5D).

FIGS. 7A-7B show the amino acid sequences of a number of PKal mutants (catalytic domain), which were produced in Pichia cells. The sequences, from top to bottom, correspond to SEQ ID NOS: 23-27.

DETAILED DESCRIPTION OF THE INVENTION

Figure 1A:
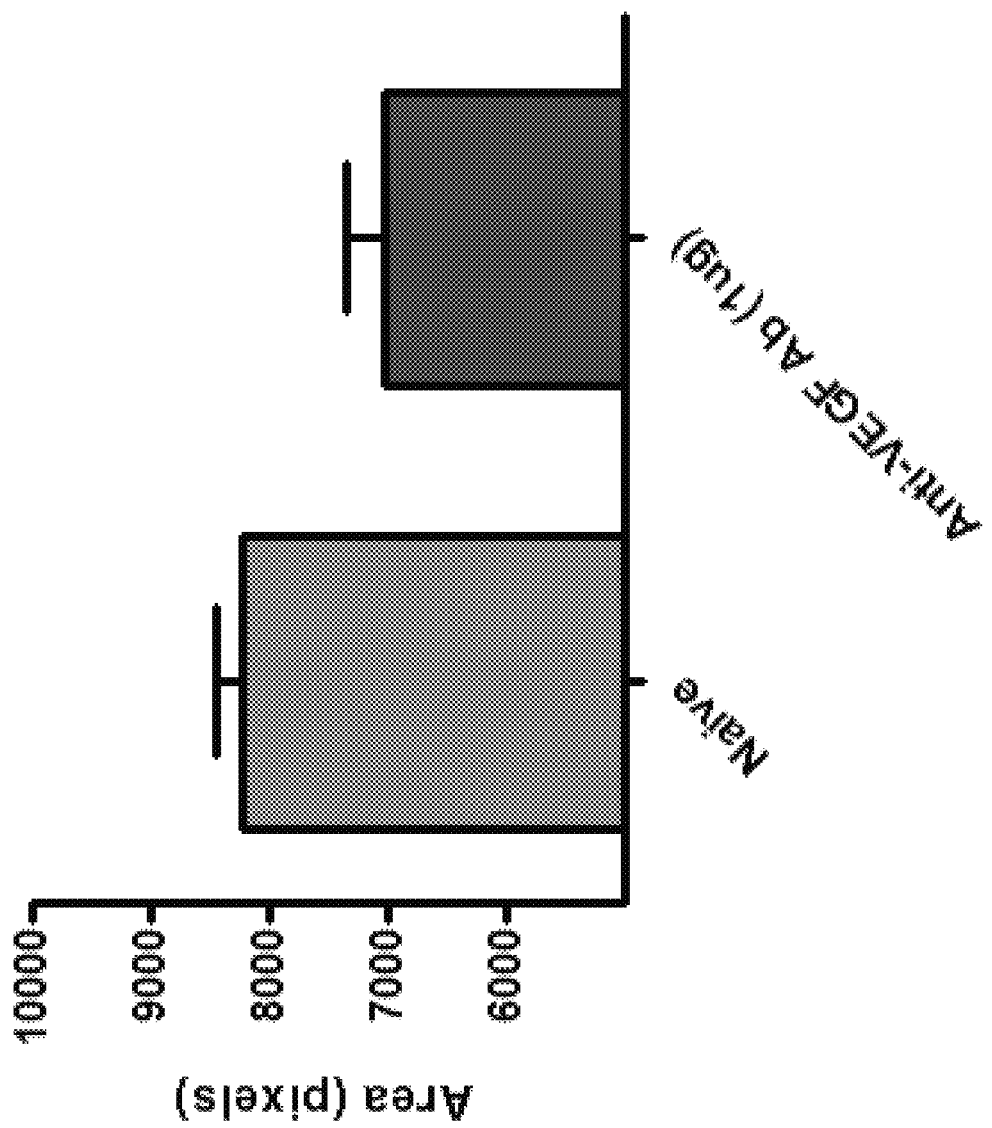
FIG. 1A shows the reduction in fluorescein angiography signal in animals treated with an intra-ocular injection of an anti-VEGF antibody (n=5, p<0.05 by t-test).
Figure 1B:
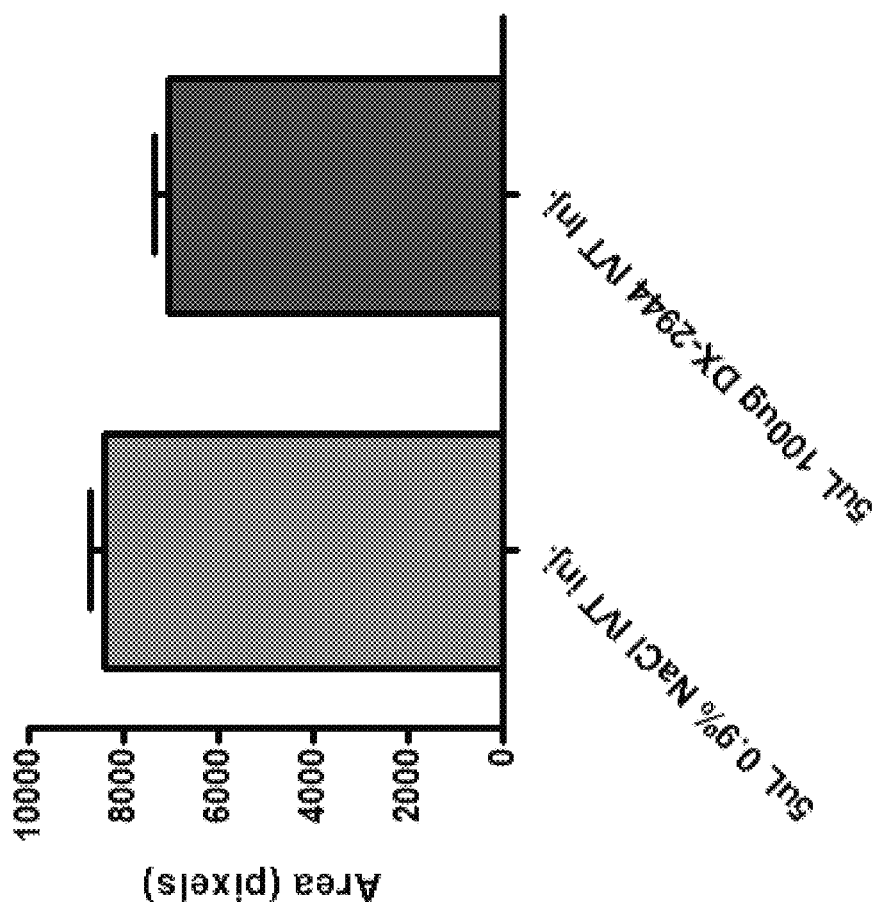
FIG. 1B shows similar reduction in signal in animals treated with DX-2944 (n=3 for the vehicle group, n=4 for the test article group, p<0.05 by t-test).
Figure 2A:
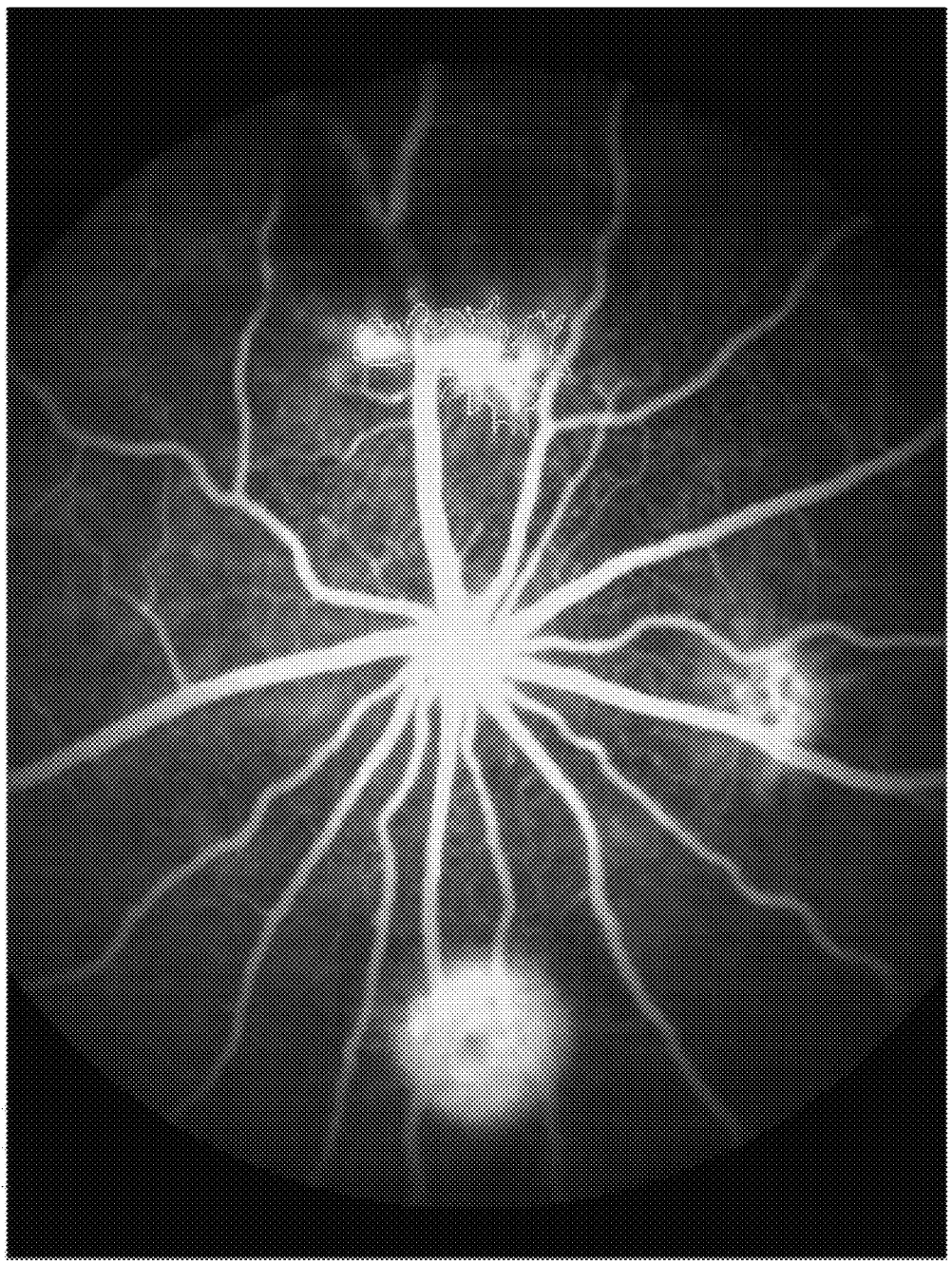
FIG. 2A shows an exemplary photograph of an eye after laser induced CNV treatment from a brown Norway rat treated with NaCl vehicle.
Figure 2B:
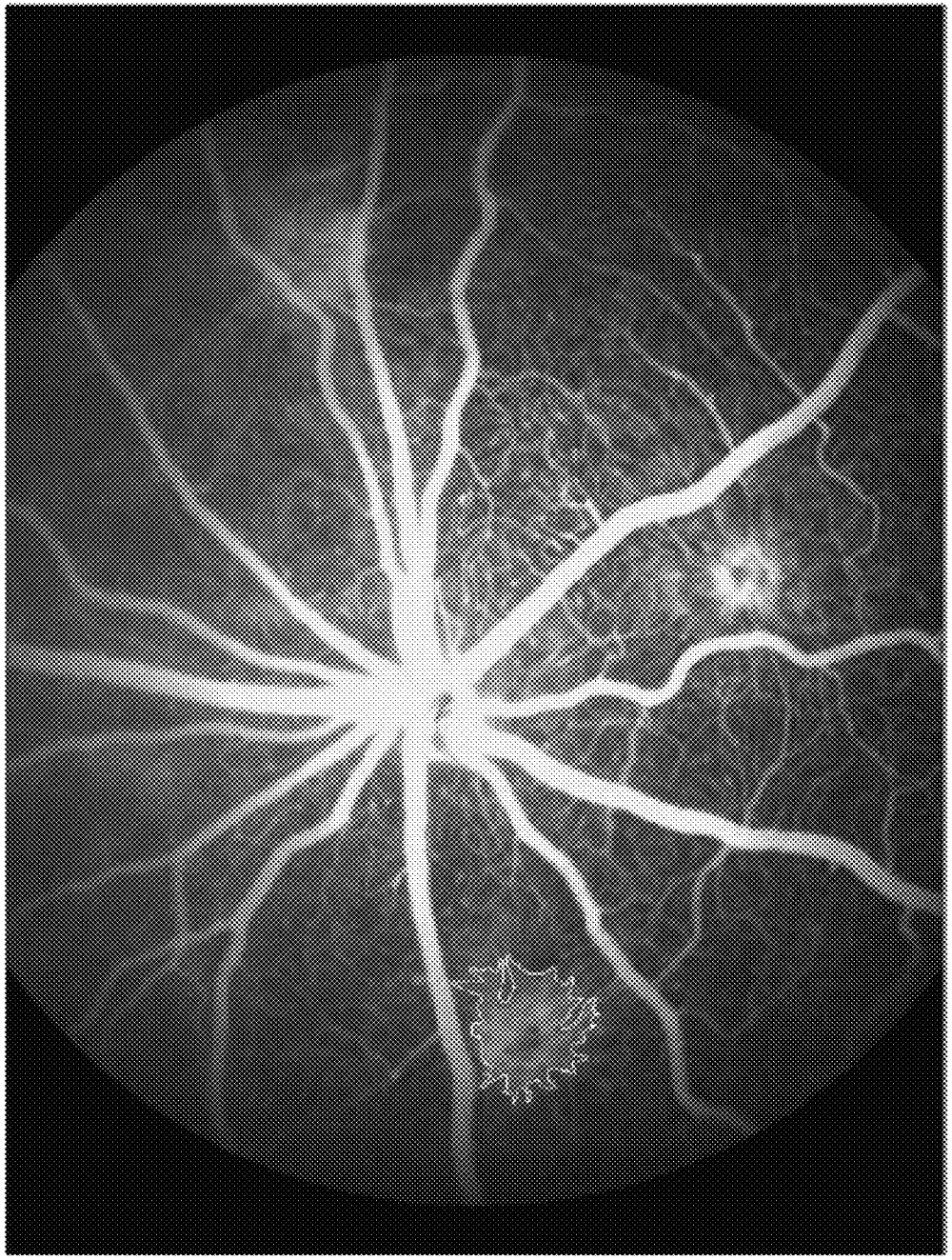
FIG. 2B shows an exemplary photograph of an eye after laser induced CNV in a brown Norway rat treated with DX-2944.
Figure 5B:
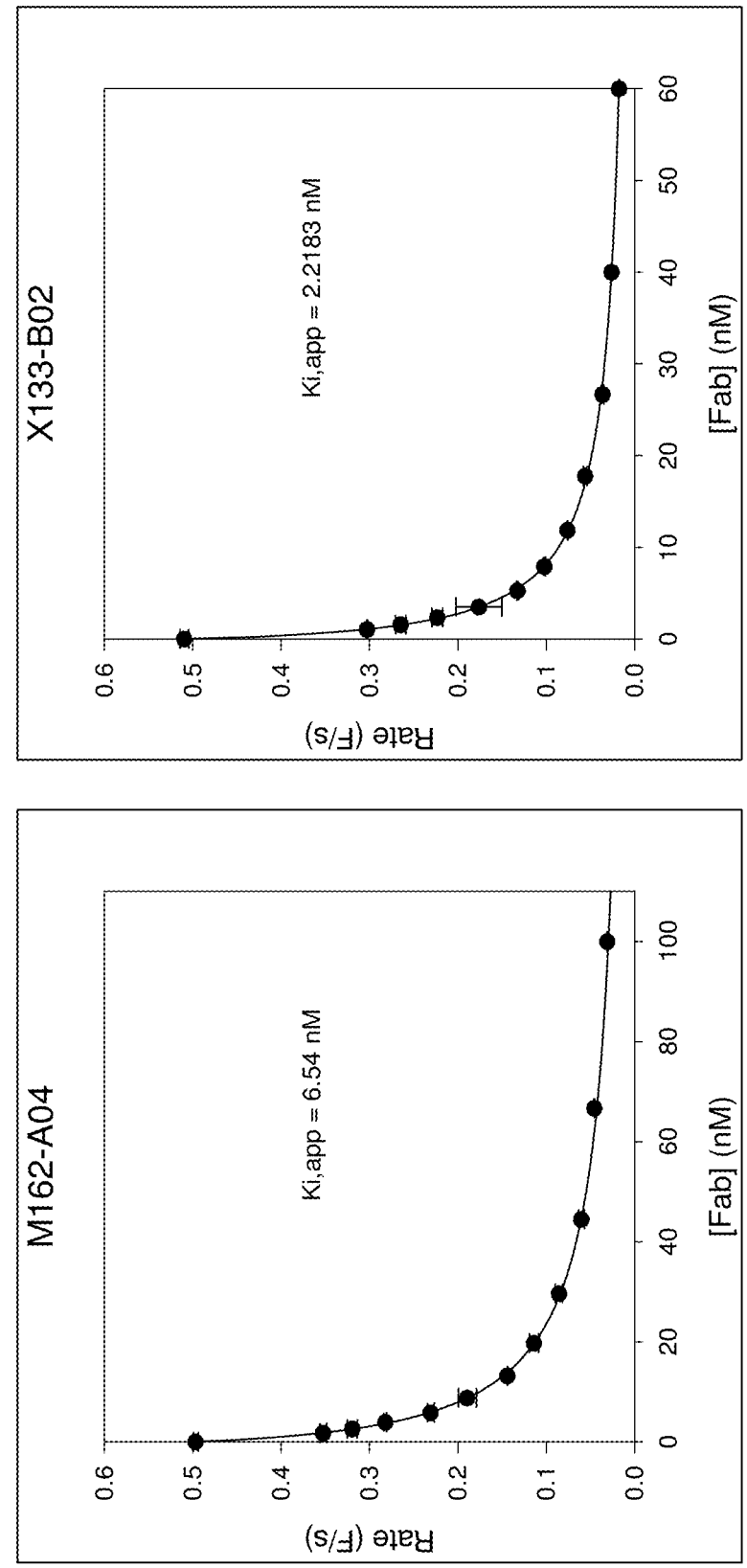
Figure 5C:
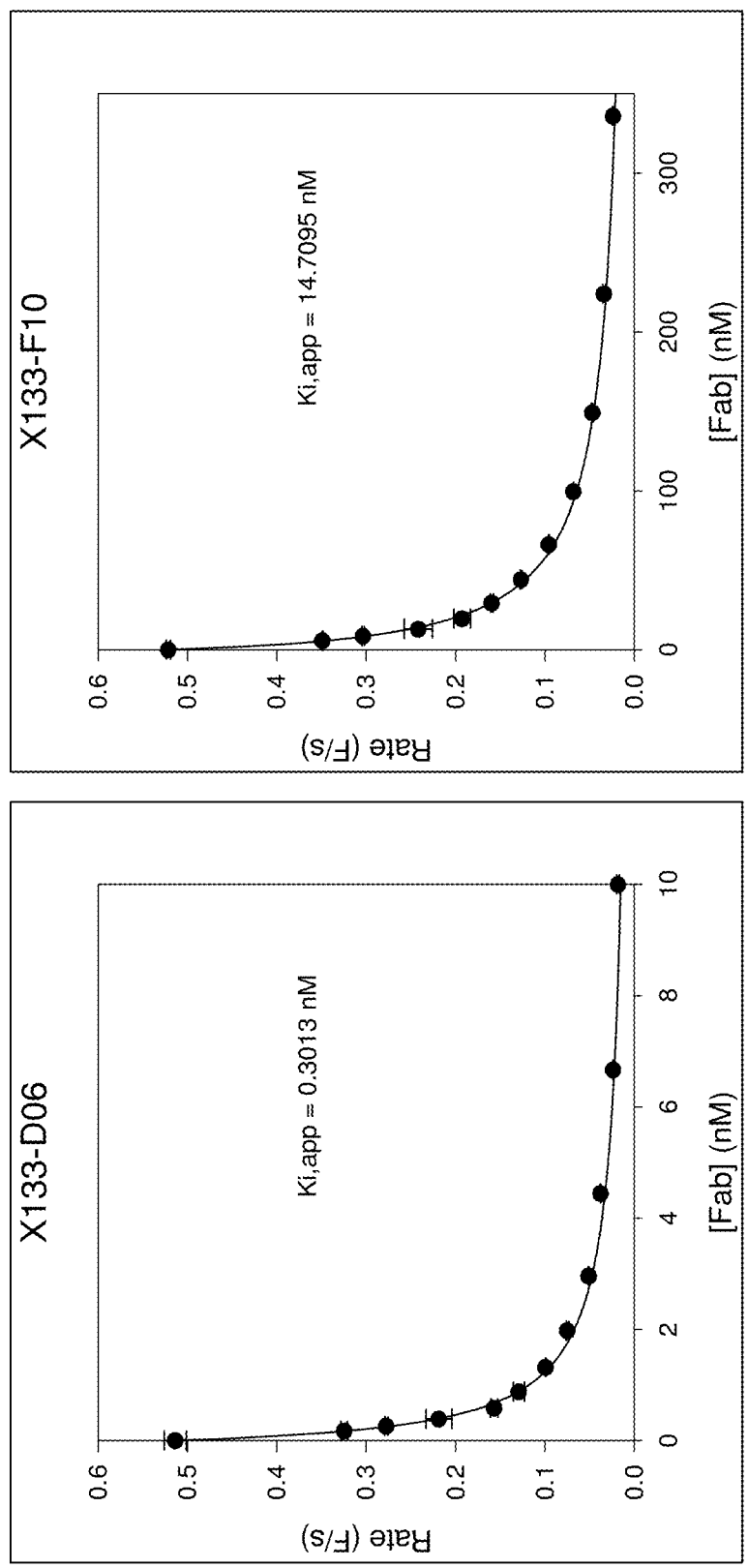
Figure 5D:
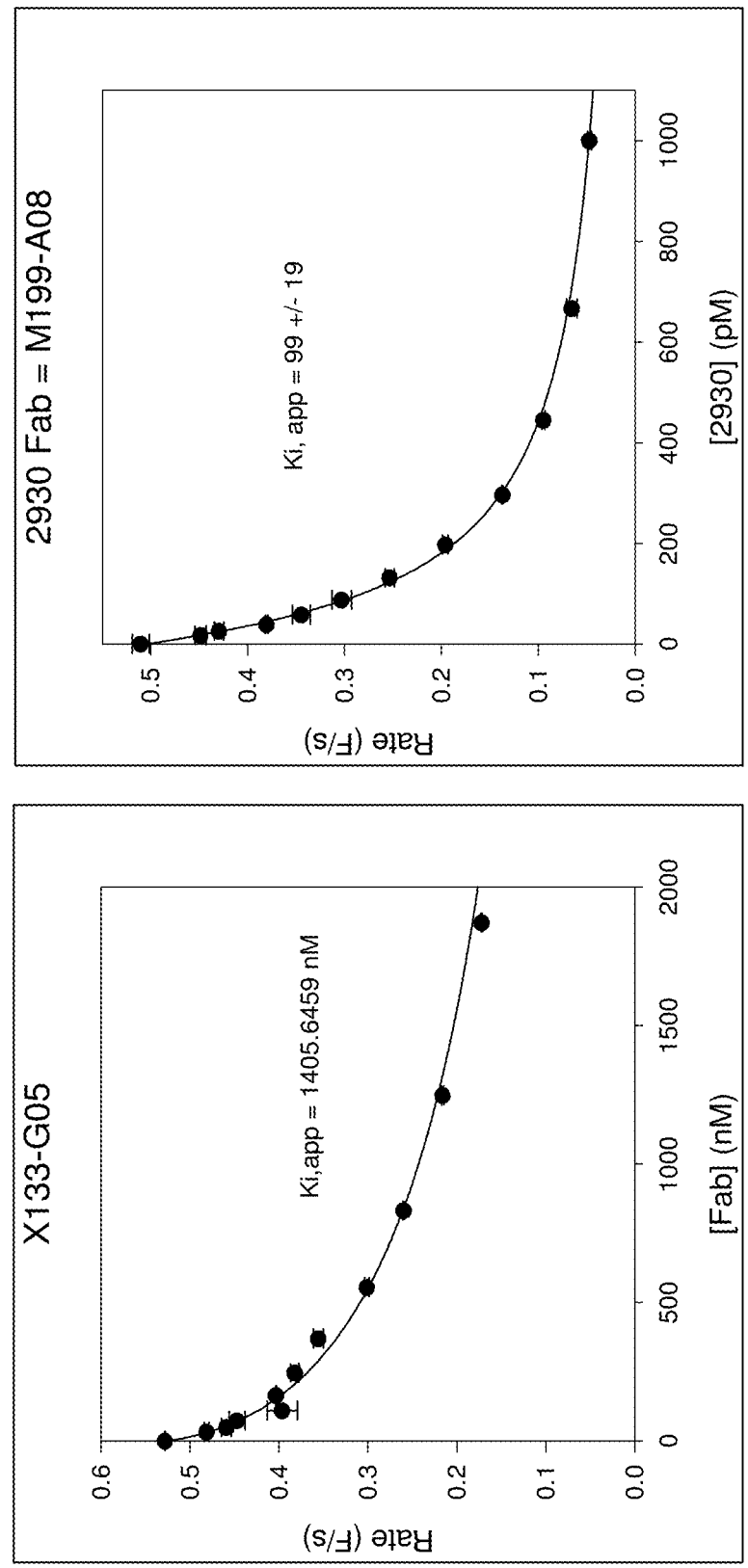

Millions of people suffer from varying degrees of vision loss due to retinal diseases, in which the delicate layer of tissue that lines the inside back of the eye is damaged, reducing its ability to send light signals to the brain. Retinal diseases may be caused by various factors, including genetic and age related factors and other diseases such as diabetes. Diabetic retinopathy is a condition that occurs in people that have diabetes, either Type I or Type II diabetes. Diabetic retinopathy is thought to be the result of hyperglycemia-induced damage to the microvasculature of the retina. This damage causes retinal blood vessels to become more permeable. In some instances, the damaged blood vessels leak fluid, proteins, and/or lipids onto the macula, which causes swelling and thickening of the macula. The swelling and thickening of the macula is referred to as diabetic macular edema (DME). Symptoms of DME include blurred vision, vision distortion, and spots in the field of vision (sometimes referred to as "floaters").

The standard treatment for DME is laser photocoagulation. This treatment has undesirable side-effects including partial loss of peripheral vision and/or night vision.

The disclosure is based, in part, a study showing that antibodies that bind to active plasma kallikrein (PKal) are therapeutically effective in an animal model of retinal diseases such as DME, AMD, RVO, uveitis, endophthalmitis, or PCV. Accordingly, in some aspects the disclosure relates to compositions and methods for the treatment of a retinal disease such as DME, AMD, RVO, uveitis, endophthalmitis, or PCV using antibodies capable of binding to active PKal (e.g., active human PKal).

Antibodies Binding to Active PKal

The present disclosure provides isolated antibodies that specifically bind active PKal, e.g., the catalytic domain of the PKal. In some embodiments, the antibody described herein does not bind to prekallikrein (e.g., human prekallikrein).

Plasma kallikrein is a serine protease component of the contact system (Sainz I. M. et al., Thromb Haemost 98, 77-83, 2007). The contact system is activated by either factor XIIa upon exposure to foreign or negatively charged surfaces or on endothelial cell surfaces by prolylcarboxypeptidases (Sainz I. M. et al., Thromb Haemost 98, 77-83, 2007). Activation of plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature.

Exemplary plasma kallikrein sequences can include human, mouse, or rat plasma kallikrein amino acid sequences, a sequence that is 80%, 85%, 90%, 95%, 96%, 97%, 98%, or 99% identical to one of these sequences, or a fragment thereof, e.g., of a sequence provided below.

An exemplary sequence of a mature human plasma kallikrein is shown below (see, e.g., Tang et al. (2005) Expression, Crystallization, and Three-dimensional Structure of the Catalytic Domain of Human Plasma Kallikrein. J of Biol Chem. 280(49): 41077-41089, which is incorporated herein by reference). This exemplary sequence comprises one mutation ($S^{484}$; in boldface) to facilitate production of a homogenous product.

```
                                        (SEQ ID NO: 11)
GCLTQLYENAFFRGGDVASMYTPNAQYCQMRCTFHPRCLLFSFLPASSIND

MEKRFGCFLKDSVTGTLPKVHRTGAVSGHSLKQCGHQISACHRDIYKGVDM

RGVNFNVSKVSSVEECQKRCTSNIRCQFFSYATQTFHKAEYRNNCLLKYSP

GGTPTAIKVLSNVESGFSLKPCALSEIGCHMNIFQHLAFSDVDVARVLTPD

AFVCRTICTYHPNCLFFTFYTNVWKIESQRNVCLLKTSESGTPSSSTPQEN
```

TISGYSLLTCKRTLPEPCHSKIYPGVDFGGEELNVTFVKGVNVCQETCTKM

IRCQFFTYSLLPEDCKEEKCKCFLRLSMDGSPTRIAYGTQGSSGYSLRLCN

TGDNSVCTTKTSTR/IVGGTNSSWGEWPWQVSLQVKLTAQRHLCGGSLIGH

QWVLTAAHCFDGLPLQDVWRIYSGILNLSDITKDTPFSQIKEIIIHQNYKV

SEGNHDIALIKLQAPLNYTEFQKPISLPSKGDTSTIYTNCWVTGWGFSKEK

GEIQNILQKVNIPLVTNEECQKRYQDYKITQRMVCAGYKEGGKDACKGDSG

GPLVCKHNGMWRLVGITSWGEGCARREQPGVYTKVAEYMDWILEKTQSSDG

KAQMQSPA

Factor XIIa activates prekallikrein by cleaving the polypeptide sequence at a single site (between Arg371-Ile372, cleavage site marked by "/" in the sequence above) to generate active plasma kallikrein, which then consists of two disulfide linked polypeptides; a heavy chain of approximately 52 kDa and a catalytic domain of approximately 34 kDa [Colman and Schmaier, (1997) "Contact System: A Vascular Biology Modulator With Anticoagulant, Profibrinolytic, Antiadhesive, and Proinflammatory Attributes" Blood, 90, 3819-3843].

Exemplary human, mouse, and rat prekallikrein amino acid sequences (including signal peptides) are illustrated below. The sequences of prekallikrein are the same as plasma kallikrein, except that active plasma kallikrein (pKal) has the single polypeptide chain cleaved at a single position (indicated by the "/") to generate two chains. The sequences provided below are full sequences that include signal sequences. On secretion from the expressing cell, it is expected that the signal sequences are removed.

Human plasma kallikrein (ACCESSION: NP_000883.2)
>gi|78191798|ref|NP_000883.2| plasma kallikrein
B1 precursor [Homo sapiens]
(SEQ ID NO: 12)
MILFKQATYFISLFATVSCGCLTQLYENAFFRGGDVASMYTPNAQYCQM

RCTFHPRCLLFSFLPASSINDMEKRFGCFLKDSVTGTLPKVHRTGAVSG

HSLKQCGHQISACHRDIYKGVDMRGVNFNVSKVSSVEECQKRCTSNIRC

QFFSYATQTFHKAEYRNNCLLKYSPGGTPTAIKVLSNVESGFSLKPCAL

SEIGCHMNIFQHLAFSDVDVARVLTPDAFVCRTICTYHPNCLFFTFYTN

VWKIESQRNVCLLKTSESGTPSSSTPQENTISGYSLLTCKRTLPEPCHS

KIYPGVDFGGEELNVTFVKGVNVCQETCTKMIRCQFFTYSLLPEDCKEE

KCKCFLRLSMDGSPTRIAYGTQGSSGYSLRLCNTGDNSVCTTKTSTR/I

VGGTNSSWGEWPWQVSLQVKLTAQRHLCGGSLIGHQWVLTAAHCFDGLP

LQDVWRIYSGILNLSDITKDTPFSQIKEIIIHQNYKVSEGNHDIALIKL

QAPLNYTEFQKPICLPSKGDTSTIYTNCWVTGWGFSKEKGEIQNILQKV

NIPLVTNEECQKRYQDYKITQRMVCAGYKEGGKDACKGDSGGPLVCKHN

GMWRLVGITSWGEGCARREQPGVYTKVAEYMDWILEKTQSSDGKAQMQS

PA

Mouse plasma kallikrein (ACCESSION: NP_032481.1)
>gi|6680584|ref|NP_032481.1| kallikrein B,
plasma 1 [Mus musculus]
(SEQ ID NO: 14)
MILFNRVGYFVSLFATVSCGCMTQLYKNTFFRGGDLAAIYTPDAQYCQK

MCTFHPRCLLFSFLAVTPPKETNKRFGCFMKESITGTLPRIHRTGAISG

HSLKQCGHQISACHRDIYKGLDMRGSNFNISKTDNIEECQKLCTNNFHC

QFFTYATSAFYRPEYRKKCLLKHSASGTPTSIKSADNLVSGFSLKSCAL

SEIGCPMDIFQHSAFADLNVSQVITPDAFVCRTICTFHPNCLFFTFYTN

EWETESQRNVCFLKTSKSGRPSPPIPQENAISGYSLLTCRKTRPEPCHS

KIYSGVDFEGEELNVTFVQGADVCQETCTKTIRCQFFIYSLLPQDCKEE

GCKCSLRLSTDGSPTRITYGMQGSSGYSLRLCKLVDSPDCTTKINAR/I

VGGTNASLGEWPWQVSLQVKLVSQTHLCGGSIIGRQWVLTAAHCFDGIP

YPDVWRIYGGILSLSEITKETPSSRIKELIIHQEYKVSEGNYDIALIKL

QTPLNYTEFQKPICLPSKADTNTIYTNCWVTGWGYTKEQGETQNILQKA

TIPLVPNEECQKKYRDYVINKQMICAGYKEGGTDACKGDSGGPLVCKHS

GRWQLVGITSWGEGCGRKDQPGVYTKVSEYMDWILEKTQSSDVRALETS

SA

Rat plasma kallikrein (ACCESSION: NP_036857.2)
>gi|162138905|ref|NP_036857.2| kallikrein B,
plasma 1 [Rattus norvegicus]
(SEQ ID NO: 13)
MILFKQVGYFVSLFATVSCGCLSQLYANTFFRGGDLAAIYTPDAQHCQK

MCTFHPRCLLFSFLAVSPTKETDKRFGCFMKESITGTLPRIHRTGAISG

HSLKQCGHQLSACHQDIYEGLDMRGSNFNISKTDSIEECQKLCTNNIHC

QFFTYATKAFHRPEYRKSCLLKRSSSGTPTSIKPVDNLVSGFSLKSCAL

SEIGCPMDIFQHFAFADLNVSHVVTPDAFVCRTVCTFHPNCLFFTFYTN

EWETESQRNVCFLKTSKSGRPSPPIIQENAVSGYSLFTCRKARPEPCHF

KIYSGVAFEGEELNATFVQGADACQETCTKTIRCQFFTYSLLPQDCKAE

GCKCSLRLSTDGSPTRITYEAQGSSGYSLRLCKVVESSDCTTKINAR/I

VGGTNSSLGEWPWQVSLQVKLVSQNHMCGGSIIGRQWILTAAHCFDGIP

YPDVWRIYGGILNLSEITNKTPFSSIKELIIHQKYKMSEGSYDIALIKL

QTPLNYTEFQKPICLPSKADTNTIYTNCWVTGWGYTKERGETQNILQKA

TIPLVPNEECQKKYRDYVITKQMICAGYKEGGIDACKGDSGGPLVCKHS

GRWQLVGITSWGEGCARKEQPGVYTKVAEYIDWILEKIQSSKERALETS

PA

The antibodies may be used in the methods described herein, e.g., in a method of treating a retinal disease. The term "isolated antibody" used herein refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC. In some examples, the antibody disclosed herein specifically binds active PKal or an epitope therein.

An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to human active PKal or an epitope therein is an antibody that binds this target antigen with greater affinity, avidity, more readily, and/or with greater duration than it binds to other antigens or other epitopes in the same antigen. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies described herein may also inhibit the activity of PKal. In some instances, the antibodies described herein can inhibit the activity of PKal by at least 50%, e.g., 60%, 70%, 80%, 90%, 95%, or higher. The inhibition constant (Ki) provides a measure of inhibitor potency; it is the concentration of inhibitor required to reduce enzyme activity by half and is not dependent on enzyme or substrate concentrations. The inhibitory activity of an anti-PKal antibody can be determined by routine methods, such as the method described in Example 3 below.

In some examples, the inhibitory activity of an anti-PKal antibody is determined by the apparent Ki ($K_{i,app}$) value. The $K_{i,app}$ value of an antibody obtained at different substrate concentrations by measuring the inhibitory effect of different concentrations of the antibody on the extent of the reaction (e.g., enzyme activity); fitting the change in pseudo-first order rate constant as a function of inhibitor concentration to the Morrison equation (Equation 1) yields an estimate of the apparent Ki value. For a competitive inhibitor, the Ki is obtained from the y-intercept extracted from a linear regression analysis of a plot of $K_{i,app}$ versus substrate concentration.

$$v = v_o - v_o \left( \frac{(K_{i,app} + I + E) - \sqrt{(K_{i,app} + I + E)^2 - 4 \cdot I \cdot E}}{2 \cdot E} \right) \quad \text{Equation 1}$$

In some examples, the anti-PKal antibodies described herein have a $K_{i,app}$ value lower than 1 nM, e.g., 0.5 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, or lower. The $K_{i,app}$ value of an antibody can be estimated following the methods known in the art and described herein (Example 2).

The antibodies described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-PKal antibodies described herein have a suitable binding affinity to a PKal or the catalytic domain thereof. As used herein, "binding affinity" refers to the apparent association constant or KA. The KA is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

$$[Bound]=[N][Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the anti-PKal antibody comprises the heavy and light CDRs or the heavy and light chain variable regions of DX-2930. The sequences of the full length heavy chain and light chain of DX-2930 are shown below. The sequences of the heavy chain variable domain and the light chain variable domain are also shown below. The sequences of the CDRs of DX-2930 are shown in Table 1.

DX-2930 Heavy Chain Amino Acid Sequence
(451 amino acids)
(SEQ ID NO: 1)
EVQLLESGGGLVQPGGSLRLSCAASGFTFSHYIMMWVRQAPGKGLEWVS

GIYSSGGITVYADSVKGRFTISRDNSKNTLYLQMNSLRAEDTAVYYCAY

RRIGVPRRDEFDIWGQGTMVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHY

TQKSLSLSPG

DX-2930 Light Chain Amino Acid Sequence
(213 amino acids, 23419.08 Da)
(SEQ ID NO: 2)
DIQMTQSPSTLSASVGDRVTITCRASQSISSWLAWYQQKPGKAPKLLIY

KASTLESGVPSRFSGSGSGTEFTLTISSLQPDDFATYYCQQYNTYWTFG

QGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

DX-2930 Heavy Chain Variable Domain Amino
Acid Sequence
(SEQ ID NO: 3)
EVQLLESGGGLVQPGGSLRLSCAASGFTFSHYIMMWVRQAPGKGLEWVS

GIYSSGGITVYADSVKGRFTISRDNSKNTLYLQMNSLRAEDTAVYYCAY

RRIGVPRRDEFDIWGQGTMVTVSS

DX-2930 Light Chain Variable Domain Amino
Acid Sequence
(SEQ ID NO: 4)
DIQMTQSPSTLSASVGDRVTITCRASQSISSWLAWYQQKPGKAPKLLIY

KASTLESGVPSRFSGSGSGTEFTLTISSLQPDDFATYYCQQYNTYWTFG

QGTKVEIK

TABLE 1

| CDRs for DX-2930. | |
|---|---|
| CDR | Amino acid sequence |
| Heavy chain CDR1 | HYIMM (SEQ ID NO: 5) |
| Heavy chain CDR2 | GIYSSGGITVYADSVKG (SEQ ID NO: 6) |
| Heavy chain CDR3 | RRIGVPRRDEFDI (SEQ ID NO: 7) |
| Light chain CDR1 | RASQSISSWLA (SEQ ID NO: 8) |
| Light chain CDR2 | KASTLES (SEQ ID NO: 9) |
| Light chain CDR3 | QQYNTYWT (SEQ ID NO: 10) |

In some embodiments, the anti-PKal antibody is a Fab comprising the same CDRs or the heavy and light chain variable regions of DX-2930. For example, DX-2944, described in Example 1 below, is the Fab portion of DX-2930.

DX-2930 is a fully human IgG derived from parent clone M0162-A04. The amino acid sequences of the $V_H$ and $V_L$ of M0162-A04 are shown in FIG. 3. Their alignment with the corresponding germline VH gene (VH3_3-23) and VL gene (VK1_L12) is also shown in FIG. 3. Compared to the HC CDR3 of M0162-A04, the HC CDR3 of DX-2930 includes the variations of T101I, I103V, and A108E (see Table 3 below; the HC CDR3 of DX-2930 being identical to M0199-A08). The Chothia Numbering Scheme is used in the present disclosure. www.bioinf.org.uk/abs/.

Table 2 below provides structural information of DX-2930, its parent antibody M0162-A04, and variants thereof.

TABLE 2

Sequence Properties of DX-2930 Variants

| Name | Properties |
| --- | --- |
| M162-A04 | This is the parent antibody of DX-2930 that was discovered in the initial phage display selection efforts (Ki, app = 2.5 nM). This antibody differs from DX-2930 at 3 critical amino acids in the CDR3 of the heavy chain and the germlined positions. |
| M199-A08 | Fab discovered following the affinity maturation of M0162-A04 using the Hv-CDR3 spiking method (Ki, app ~0.06 nM). This antibody shares the same amino acids in the variable region with DX-2930 but was not germlined and does not contain a Fc fragment. |
| X115-F02 | Fully human IgG, kappa light chain 1 amino acid in the light chain was mutated to their germline sequence. The DNA sequence of X115-F02 was optimized for expression in CHO cells Expressed transiently in 293T cells following subcloning into the pRH1-CHO vector |
| DX-2930 | Fully human IgG, kappa light chain 1 amino acid in the light chain and 2 amino acids in the heavy were mutated to their germline sequence. The DNA sequence of DX-2930 was optimized for expression in CHO cells and cloned into the pEhl vector for stable expression using the glutamate synthase system. The Fc of DX-2930 was modified to remove the C-terminal lysine reside, in order to obtain a more homogeneous product. |
| DX-2944 | This antibody is a Fab of DX-2930 |

Antibodies Targeting Specific Residues in Human Plasma Kallikrein

In some embodiments, the antibody that specifically binds to active PKal interacts with one or more of the residues (e.g., at least 3, 5, 8, 10, 15, 20, 25, 30, 35, 40, or 45) in the catalytic domain of human PKal, including V410, L412, T413, A414, Q415, R416, L418, C419, H434, C435, F436, D437, G438, L439, W445, Y475, K476, V477, S478, E479, G480, D483, F524, E527, K528, Y552, D554, Y555, A564, D572, A573, C574, K575, G576, S578, T596, S597, W598, G599, E600, G601, C602, A603, R604, Q607, P608, G609, V610, and/or Y611 (numbers based on the full length prekallikrein amino acid sequence). The positions of these residues are indicated in FIG. 4 (boldfaced and underlined). These residues are identified as interacting with one or more residues in DX-2930 according to the crystal structures described in Example 2 below.

Interacting means that the distance between two residues in a complex formed by two binding partners is lower than a predetermined value, e.g., <6 Å, <4 Å, or <2 Å. For example, an interacting residue in one binding partner can have has at least 1 atom within a given threshold (e.g., <6 Å, <4 Å, or <2 Å) of at least 1 atom from a residue of the other binding partner on the complexed structure. Interacting does not require actual binding. Interacting residues are suggested as involved in antibody recognition.

In some embodiments, the antibodies described herein bind human active PKal at an epitope comprising one or more of the residues listed above. An "epitope" refers to the site on a target compound that is bound by an antibody such as a Fab or full length antibody. An epitope can be linear, which is typically 6-15 aa in length. Alternatively, the epitope can be conformational.

In some examples, the antibody that specifically binds to active PKal described herein binds an epitope that comprises the following segments: V410-C419, H434-L439, Y475-G480, F524-K528, Y552-Y555, D572-S578, T596-R604, or Q607-Y611. In some examples, the antibody (e.g., a non-DX-2930 antibody) binds the same epitope as DX-2930 or competes for binding to the active PKal as DX-2930.

In one example, the anti-PKal antibodies described herein preferentially bind wild-type Pkal as compared to a mutant that includes mutations at one or more of R551, Q553, Y555, T558, and R560, e.g., Mutant 2 described in Example 4. Such antibodies may bind wild-type PKal at a much higher affinity as compared to the mutant (e.g., at least 2-fold, 5-fold, 10-fold, 50-fold, 100-fold, 200-fold, 500-fold, 1,000-fold higher). Alternatively or in addition, the antibodies exhibit a much higher inhibitory activity against the wild-type pKal as relative to the mutant (e.g., at least 2-fold, 5-fold, 10-fold, 50-fold, 100-fold, 200-fold, 500-fold, 1,000-fold higher).

In other examples, the anti-PKal antibodies described herein binds wild-type active PKal and functional variants thereof. The antibody can preferentially bind an active PKal as relative to its binding to an inactive mutant. The antibody can preferentially bind active PKal as relative to prekallikrein.

Anti-Plasma Kallikrein Antibodies Having Specific Motifs and/or Residues

In some embodiments, the anti-PKal antibody described herein comprises a $V_H$ and a $V_L$, each of which comprises three CDRs flanked by framework regions (FR1-CDR1-FR2-CDR2-FR3-CDR3-FR4; see FIG. 3). The CDR3 of the heavy chain can comprise the motif: $X99R_{100}X_{101}G_{102}X_{103}P_{104}R_{105}X_{106}X_{107}X_{108}X_{109}X_{110}X_{111}$, in which $X_{99}$ is R or Q, $X_{101}$ is T, I, R, S, or P, $X_{103}$ is V, I, L, $X_{106}$ is R or W, $X_{107}$ is D or N, $X_{108}$ is A, S, D, E, or V, $X_{109}$ is F or L, $X_{110}$ is D, E, or N, and $X_{111}$ is I, N, M, or S (SEQ ID NO:15). In some examples, $X_{99}$ is Q and $X_{101}$ is I, R, S, or P. Alternatively or in addition, X106 is W and $X_{111}$ is N, M, or S. In other examples, $X_{101}$ is I, $X_{108}$ is E, and $X_{103}$ is I or L; or $X_{101}$ is I and $X_{103}$ is I or L. In yet other examples, $X_{103}$ is I or L and $X_{110}$ is D, E, or N.

In addition, such an anti-pKal antibody can include one or more other residues that are identified based on the crystal structures discussed herein as being involved in interacting with the catalytic domain of human PKal. These residues can be located in the $V_H$ or the $V_L$ chain. Examples include E1, V2, F27, T28, F29, and S30 in the FR1 of the $V_H$, H31 in the HC CDR1; S31 and W32 in the LC CDR1, Y49 in the FR1 of the $V_L$ chain, K50, T53, L54, and E55, and S56 in LC CDR2, and G57 and V58 the FR3 of the $V_L$ chain. The anti-PKal antibodies as described above can use any germline heavy chain and light chain V genes as the framework. Heavy chain V genes include, but are not limited to, IGHV1-2, IGHV1-3, IGHV1-8, IGHV1-18, IGHV1-24, IGHV1-45, IGHV1-46, IGHV1-58, IGHV1-69, IGHV2-5, IGHV2-26, IGHV2-70, IGHV3-7, IGHV3-9, IGHV3-11, IGHV3-13, IGHV3-15, IGHV3-20, IGHV3-21, IGHV3-23, IGHV3-30, IGHV3-33, IGHV3-43, IGHV3-48, IGHV3-49, IGHV3-53, IGHV3-64, IGHV3-66, IGHV3-72, IGHV3-73, IGHV3-74, IGHV4-4, IGHV4-28, IGHV4-31, IGHV4-34, IGHV4-39, IGHV4-59, IGHV4-61, IGHV4-B, IGHV5-51, IGHV6-1, and IGHV7-4-1.

In some examples, the antibody uses a κ light chain. Light chain VK genes include, but are not limited to, V genes for IGKV1-05, IGKV1-06, IGKV1-08, IGKV1-09, IGKV1-12, IGKV1-13, IGKV1-16, IGKV1-17, IGKV1-27, IGKV1-33, IGKV1-37, IGKV1-39, IGKV1D-16, IGKV1D-17, IGKV1D-43, IGKV1D-8, IGKV2-24, IGKV2-28, IGKV2-29, IGKV2-30, IGKV2-40, IGKV2D-26, IGKV2D-29, IGKV2D-30, IGKV3-11, IGKV3-15, IGKV3-20, IGKV3D-07, IGKV3D-11, IGKV3D-20, IGKV4-1, IGKV5-2, IGKV6-21, and IGKV6D-41. In other examples, the antibody uses a λ light chain, e.g., any of IGLV1-IGLV10.

The antibody also can use any germline heavy J segment (e.g., heavy chain IGJH1-IGJH6) and light chain J segment (e.g., IGJK1, IGJK2, IGJK3, IGJK4, or IGJK5), which can subject to variations, such as deletions at the C-terminus, N-terminus, or both.

Germline antibody gene/segment sequences are well known in the art. See, e.g., www.vbase2.org/vbstat.php.

In some examples, the anti-PKal antibody described herein uses VH3_3-23 and/or VK1_L12 as the framework for the heavy chain and/or the light chain. It may include substantially similar HC CDR1, HC CDR2, and/or HC CDR3, and LC CDR1, LC CDR2, and/or LC CDR3 as those in M0162-A04 (FIG. 3), e.g., containing up to 5, 4, 3, 2, or 1 amino acid residue variations as compared to the corresponding CDR region in M0162-A04.

In other examples, the anti-PKal antibody comprises a $V_H$ chain that includes a $V_H$ CDR1, $V_H$ CDR2, and VH CDR3 at least 75% (e.g., 80%, 85%, 90%, 95%, or 98%) identical to the corresponding $V_H$ CDRs of M0162-A04, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_L$ CDRs of M0162-A04.

Alternatively, the anti-PKal antibody comprises a $V_H$ chain at least 75% (e.g., 80%, 85%, 90%, 95%, or 98%) identical to the $V_H$ chain (mature or precursor) of M0162-A04 and/or a $V_L$ chain at least 75% (e.g., 80%, 85%, 90%, 95%, or 98%) identical to the $V_L$ chain (mature of precursor) of M0162-A04.

The "percent identity" of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some instances, conservative mutations can be introduced into the CDRs in M0162-A04, e.g., at positions where the residues are not likely to be involved in interacting with PKal as determined based on the crystal structure. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Use of Anti-PKal Antibodies for Treating Diabetic Macular Edema (DME)

Aspects of the disclosure relate to treatment of subject having, suspected of having, or at risk for having a retinal disease, for example, DME, AMD, RVO, uveitis, endophthalmitis, or PCV. In some embodiments, methods for treating such subjects are provided, in which a composition comprising an effective amount of an antibody that specifically binds to active PKal as described herein is administered to the subject via a suitable route.

To practice a method disclosed herein, an effective amount of a composition (e.g., a pharmaceutical composition) described herein can be administered to a subject (e.g., a human) in need of the treatment via a suitable route, such as intravenous administration (e.g., as a bolus or by continuous infusion over a period of time), by intraocular injection, intravitreal injection, or subcutaneous injection. The composition may comprise one or more antibodies binding to active human PKal. Alternatively, the composition may comprise nucleic acid(s) encoding the anti-PKal antibody, which may be in operable linkage to a suitable promoter. Such a nucleic acid may be an expression vector.

The subject to be treated by the compositions and methods described herein can be a mammal, more preferably a human, e.g., a human having diabetes. Mammals include, but are not limited to, farm animals, sport animals, pets, primates, horses, dogs, cats, mice and rats. A human subject who needs the treatment may be a human patient having, at risk for, or suspected of having a retinal disease, including DME, AMD, RVO, uveitis, endophthalmitis, or PCV. Age-related macular degeneration (AMD) is a deterioration or breakdown of the eye's macula. With macular degeneration, a subject may have symptoms such as blurriness, dark areas or distortion in the central vision, and optionally permanent loss of the central vision. Retinal vein occlusion (RVO) is a blockage of the small veins that carry blood away from the retina. It is often caused by hardening of the arteries (atherosclerosis) and the formation of a blood clot. Diabetic macular edema (DME) is the proliferative form of diabetic retinopathy characterized by swelling of the retinal layers, neovascularization, vascular leak, and retinal thickening in diabetes mellitus due to leaking of fluid from blood vessels within the macula. Polypoidal choroidal vasculopathy (PCV) is a disease of the choroidal vasculature. It is present in both men and woman of many ethnicities, characterized by serosanguineous detachments of the pigmented epithelium and exudative changes that can commonly lead to subretinal fibrosis. Uveitis is swelling and irritation of the uvea, the middle layer of the eye. The uvea provides most of the blood supply to the retina. It can be caused by autoimmune disorders, including rheumatoid arthritis or ankylosing spondylitis. It can also be caused by infection or exposure to toxins. In many cases, the cause is unknown. Endophthalmitis is an inflammatory condition of the intraocular cavities (ie, the aqueous and/or vitreous humor) usually caused by infection.

A subject having such a retinal disease can be identified by routine medical examination, e.g., a visual acuity test, tonometry, optical coherence tomography, color stereo fundus photography, a fluorescein angiogram, or combinations thereof. A subject suspected of having the retinal disease might show one or more symptoms of the disease, e.g., blurred vision, distorted vision, or spots in the field of vision. A subject at risk for the retinal disease can be a subject having one or more of the risk factors. For example, a subject at risk for DME may have one or more of the following risk factors: hypertension, fluid retention, hypoalbuminemia, or hyperlipidemia. Risk factors associated with RVO include atherosclerosis, diabetes, high blood pressure (hypertension), and other eye conditions, such as glaucoma, macular edema, or vitreous hemorrhage.

In some embodiments, a subject may be treated with an antibody as described herein in combination with another treatment for DME. Non-limiting examples of treatment for DME include laser photocoagulation, steroids, VEGF pathway targeting agents (e.g., Lucentis® (ranibizumab) or Eylea® (aflibercept)), and/or anti-PDGF agents.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of DME. Alternatively, sustained continuous release formulations of an anti-PKal may be appropriate. Various formulations and devices for achieving sustained release are known in the art.

In one example, dosages for an anti-PKal antibody as described herein may be determined empirically in individuals who have been given one or more administration(s) of the antibody. Individuals are given incremental dosages of the antibody. To assess efficacy of the antibody, an indicator of a retinal disease be followed.

Generally, for administration of any of the antibodies described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate DME, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an anti-PKal antibody will depend on the specific antibody (or compositions thereof) employed, the type and severity of the retinal disease (e.g., DME, AMD, RVO, uveitis, endophthalmitis, or PCV), whether the antibody is administered for preventive or therapeutic purposes, previous therapy, the patient's clinical history and response to the antibody, and the discretion of the attending physician. Typically the clinician will administer an anti-PKal antibody, until a dosage is reached that achieves the desired result. Administration of an anti-PKal antibody can be continuous or intermittent, depending, for example, upon the recipient's physiological condition, whether the purpose of the administration is therapeutic or prophylactic, and other factors known to skilled practitioners. The administration of an anti-PKal antibody may be essentially continuous over a preselected period of time or may be in a series of spaced dose, e.g., either before, during, or after developing the retinal disease.

As used herein, the term "treating" refers to the application or administration of a composition including one or more active agents to a subject, who has DME, a symptom of a retinal disease (e.g., DME, AMD, RVO, uveitis, endophthalmitis, or PCV), or a predisposition toward the retinal disease, with the purpose to cure, heal, alleviate, relieve, alter, remedy, ameliorate, improve, or affect the retinal disease, the symptom of the disease, or the predisposition toward the disease.

Alleviating a retinal disease such as DME, AMD, RVO, uveitis, endophthalmitis, or PCV, includes delaying the development or progression of the disease, or reducing disease severity. Alleviating the disease does not necessarily require curative results. As used therein, "delaying" the development of a retinal disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a retinal disease includes initial onset and/or recurrence.

In some embodiments, the anti-PKal antibody described herein is administered to a subject in need of the treatment at an amount sufficient to inhibit the activity of active PKal by at least 20% (e.g., 30%, 40%, 50%, 60%, 70%, 80%, 90% or greater) in vivo. In other embodiments, the antibody is administered in an amount effective in reducing the PKal level by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes intravitreal, subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some embodiments, the composition as described herein is administered into an eye of a patient where treatment is needed. In one example, it is administered topically. In another example, it is injected intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an anti-PKal antibody is administered via site-specific or targeted local delivery techniques. Examples of site-specific or targeted local delivery techniques include various implantable depot sources of the anti-PKal antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the anti-PKal antibodies described herein) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

Anti-PKal antibodies described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history. In some embodiments, more than one anti-PKal antibodies, or a combination of an anti-PKal antibody and another suitable therapeutic agent, may be administered to a subject in need of the treatment. The antagonist can be the same type or different from each other. The anti-PKal antibody can also be used in conjunction with other agents that serve to enhance and/or complement the effectiveness of the agents.

Treatment efficacy for a retinal disease can be assessed by methods well-known in the art, e.g., by fluorescein angiography.

Antibody Preparation

Antibodies capable of binding PKal as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., a human PKal or the catalytic domain thereof) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-PKal monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the PKal activity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOLI, or $R1N=C=NR$, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of PKal. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455, and. Alternatively, the phage display technology (McCafferty et al., (1990) Nature 348:

552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab∝)2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, Fabs, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques for producing Fabs are also known in the art (see, e.g., PCT Publication Nos. WO1993006217 and WO2005038031, which are incorporated by reference herein). A variety of host-expression vector systems may be utilized to recombinantly express a Fab. Such host-expression systems represent cells which may, when transformed or transfected with the appropriate nucleotide coding sequences, express a Fab described herein. These include, but are not limited to, microorganisms such as bacteria (e.g., E. coli and B. subtilis) transformed with recombinant bacteriophage DNA, plasmid DNA or cosmid DNA expression vectors containing coding sequences encoding a Fab antibody described herein; yeast (e.g., Saccharomyces pichia) transformed with recombinant yeast expression vectors containing sequences encoding a Fab antibody described herein; insect cell systems infected with recombinant virus expression vectors (e.g., baclovirus) containing the sequences encoding a Fab antibody described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding a Fab antibody described herein; or mammalian cell systems (e.g., COS, CHO, BHK, 293, 293T, 3T3 cells, lymphotic cells harboring recombinant expression constructs encoding a Fab antibody described herein. In some embodiments, a Fab described herein is recombinantly expressed E. coli. Once a Fab has been recombinantly expressed, it may be purified by any method known in the art for purification of polypeptides or antibodies for example, by chromatography (e.g., ion exchange, affinity, or sizing column chromatography), centrifugation, differential solubility, or by any other standard technique for the purification of polypeptides or antibodies.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to a PKal can be identified from the library following routine procedures. Positive clones can be subjected to further screening to identify those that inhibits PKal activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the PKal polypeptide have been replaced (swapped) with sequences from a closely related, but antigenically distinct protein (such as another member of the neurotrophin protein family). By assessing binding of the antibody to the mutant PKal (e.g., those mutants described in Example 2 below), the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Any of the suitable methods known in the art, e.g., the epitope mapping methods as described herein, can be applied to determine whether the anti-PKal antibody binds one or more of the specific residues/segments in the PKal as described herein. Further, the interaction of the antibody with one or more of those defined residues in PKal can be determined by routine technology. For example, a crystal structure can be determined following the method disclosed in Example 1 below and the distances between the residues in PKal and one or more residues in the antibody can be determined accordingly. Based on such distance, whether a specific residue in PKal interacts with one or more residues in the antibody can be determined. Further, suitable methods, such as competition assays and target mutagenesis assays can be applied to determine the preferential binding of a candidate anti-PKal antibody to the PKal as compared to another target such as a mutant PKal.

Pharmaceutical Compositions

One or more of the above-described anti-PKal antibodies can be mixed with a pharmaceutically acceptable carrier (excipient), including buffer, to form a pharmaceutical composition for use in alleviating DME. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. In one example, a pharmaceutical composition described herein contains more than one anti-PKal antibodies that recognize different epitopes/residues of active PKal.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the anti-PKal antibody, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-PKal antibody may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation. For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing an anti-PKal antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits for Use in Treating Retinal Diseases

The present disclosure also provides kits for use in treating a retinal disease, such as DME, AMD, RVO, uveitis, endophthalmitis, or PCV. Such kits can include one or more containers comprising an anti-PKal antibody, e.g., any of those described herein, for example, DX-2944.

In some embodiments, the kit can comprise instructions for use in accordance with any of the methods described herein. The included instructions can comprise a description of administration of the anti-PKal antibody to treat, delay the onset, or alleviate a retinal disease. The kit may further comprise a description of selecting an individual suitable for treatment based on identifying whether that individual has or is at risk for the retinal disease. In still other embodiments, the instructions comprise a description of administering an antibody to an individual at risk of the target disease.

The instructions relating to the use of an anti-PKal antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as a syringe or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-PKal antibody as those described herein.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Effect of DX-2944 in a Laser Induced Choroidal Neovascularization (Laser CNV) Disease Model DX-2944 is a recombinant Fab version of DX-2930 that was expressed and purified from an *E. coli* expression system. The Laser CNV model is an established rodent model of complications associated with human retinal diseases, such as age-related macular degeneration (AMD), retinal vein occlusions, and macular edema. The experimental design used for this study is outlined below.

Experimental Design
Day 1: Bilateral Laser treatment to produce 3 lesions per eye
Day 3: Bilateral Intravitreal injection of test agent, vehicle or, positive control (anti-VEGF Ab)
Day 22: In-vivo fluorescein angiography The results in FIGS. 1A-1B and FIGS. 2A-2B indicate that DX-2944 reduces observed CNV to approximately the same extent as the positive control (an anti-VEGF antibody). The fluorescein angiography mean signal for the anti-VEGF treated group was 7023 fluorescence units, which is similar to that observed for the DX-2944 treated group at 7071 fluorescence units.

Example 2: Identification of Critical Residues in the Catalytic Domain of Human Plasma Kallikrein Based on Crystal Structures of DX-2930-PKal Complex The catalytic domain of human plasma kallikrein, fused with a His-tag, was expressed in insect cells and purified initially by a nickel affinity column. The His-tag was removed from the plasma kallikrein via trypsin digestion and the free plasma kallikrein was purified by a benzamidine affinity column, followed by a SEC column. The purified product was examined on a PAGE gel. The result indicates that the catalytic domain of human plasma kallikrein was properly expressed and purified.

DX-2930 was prepared via routine recombinant technology and purified. A recombinant Fab fragment of DX-2930 was produced via routine method and purified.

The DX-2930 Fab fragment and the catalytic domain of human plasma kallikrein were mixed at various concentrations under suitable conditions allowing formation of antibody-PKal complexes. The complexes thus formed were examined using HPLC to determine the antibody-PKal ratio in the complexes. Accordingly, the suitable concentrations of both the antibody and the PKal were identified for formation of a 1:1 complex.

The antibody-PKal complex was kept under various conditions allowing for crystallization. Diffraction analysis was performed on the crystallized complex. The crystal structures (2.1 Å and 2.4 Å) were determined based on the diffraction statistics.

According to the crystal structures, residues in the catalytic domain of human PKal that are involved in the interaction with DX-2930 were identified. These residues are indicated (boldfaced and underlined) in FIG. 4, which provides the amino acid sequence of the catalytic domain of human PKal (residues 391-638 of human PKal).

In addition, residues in DX-2930 that interact with PKal were also identified based on the crystal structure, including E1, V2, F27, T28, F29, S30, H31, R100, I101, G102, V103, P104, R105, R106, D107, G107, K108, and D111 in the heavy chain variable region, and S31, W32, Y49, K50, T53, L54, E55, S56, G57, and V58 in the light chain variable region.

These results indicate that HC CDR3 of DX-2930 is the main region that interacts with PKal and a couple of residues in the HC CDR1 and FR1 might also contribute to the interaction with PKal. In the light chain, the LC CDR2 region was found to contribute to the interaction.

Further, the results also indicate that variations at certain positions with the HC CDR3 region may be allowed. For example, position 103 requires small hydrophobic residues such as V or I. As another example, R106 may be replaced with W, and E108 may be replaced with S or D without substantially affecting the PKal binding activity. Similarly, D110 might be replaced with E.

Example 3: Affinity Maturation Results Match Structural Information Derived from Crystal Structure The heavy chain variable region, particularly the HC CDR3 region, of antibody M0162-A04 was subject to affinity maturation. Various mutants having amino acid variations at one or more positions in the HC CDR3 region were generated and their $K_{i,app}$ values were determined following routine methods.

Briefly, PKal and a Fab at various concentrations are incubated together for 1 hour at 30° C. A substrate peptide (cleavable by PKal) is then added to this PKal-Fab mixture. The rate of substrate peptide cleavage/proteolysis is then measured, and plotted against the concentrations of the Fab. This plot is then fit to the Morrison equation, which calculates the $K_{i,app}$ value. The results thus obtained are shown in FIGS. 5A-5D and Table 3 below:

TABLE 3

Summary of Hv-CDR3 Affinity Maturation Results

| Initial Name | Hv CDR3 | Ki, app (nM) | SEQ ID NO: |
|---|---|---|---|
| M0162-A04 | RRTGIPRRDAFDI | 2.5 | 28 |
| M0199-A11 | --R---------- | 2 | 29 |
| M0201-F11 | --S---------- | 3 | 30 |
| M0202-A08 | -------W----- | 2.8 | 31 |
| M0201-A06 | ---------V--- | 3.8 | 32 |
| M0202-E03 | ----------E- | 2 | 33 |
| M0199-B01 | ------------N | 1.6 | 34 |
| M0200-B01 | ------------S | 3.6 | 35 |
| M0201-H06 | ----V-------- | 0.6 | 36 |
| M0202-H05 | ----V----V--- | 0.26 | 37 |
| M0201-H08 | ----V-----L-N | 0.8 | 38 |
| M0200-E11 | ----V-------N | 0.4 | 39 |
| M0200-H07 | ----V---N---N | 0.4 | 40 |
| M0202-F06 | ----V--W----- | 0.33 | 41 |
| M0200-A10 | ----V----S--- | 0.25 | 42 |
| M0202-G03 | ----V----S-E- | 0.4 | 43 |
| M0202-A12 | Q---V----S-N- | 0.1 | 44 |
| M0202-H03 | ----V--W-D--- | 0.1 | 45 |
| M0201-A07 | ----V----E--- | 0.1 | 46 |
| M0202-C02 | --P-V-------- | 0.6 | 47 |
| M0202-B04 | --S-V-------- | 0.2 | 48 |
| M0202-E06 | --R-V----D--- | 0.06 | 49 |
| M0202-A01 | --I-V-------- | 0.3 | 50 |
| M0202-D09 | --I-V----S--- | 0.2 | 51 |
| M0200-D03 | --I-V----S--M | 0.1 | 52 |
| M0202-C09 | --I-V----D--- | 0.06 | 53 |
| M0199-A08 | --I-V----E--- | 0.06 | 7 |
| X133-B02 | --I---------- | 2.2 | 54 |
| X133-D06 | --I------E--- | 0.33 | 55 |
| X135-A01 | ----A-------- | 247.7 | 56 |
| X133-G05 | ----S-------- | 1405.6 | 57 |
| X133-F10 | ----L-------- | 14.7 | 58 |
| X135-A03 | ---------E--- | 1.1 | 59 |

The affinity maturation results indicate that variations at certain positions within the HC CDR3 region result in high affinity/inhibitory anti-PKal antibodies as compared to the parent M0162-A04 clone. These results match with the structural information provided in Example 2 above. Note that the HC CDR3 region of clone M0199-A08 is identical to that of DX-2930.

Example 4: Impact of Mutations in Plasma Kallikrein on Antibody Inhibitory Activity The inhibitory activities of mutant X115-F02 against various PKal mutants were examined.

X115-F02 is an IgG that is the same as DX-2930 except that it contains a C-terminal lysine residue not present in DX-2930 and was expressed in HEK293T cells rather than CHO cells (Table 2 above). The binding specificity and affinity of X115-F02 is the same as DX-2930.

The wild type and four mutants of plasma kallikrein used in this study (FIGS. 7A-7B) are recombinant catalytic domains expressed and purified from *Pichia pastoris*. Mutant 1 contains the following mutations in the S3 subsite of the active site: S478A, N481A, S506A, Y507A) (numbers based on the full length prekallikrein amino acid sequence). Mutant 2 contains the following mutations in the S1' subsite of the active site: R551A, Q553A, Y555A, T558A, R560A. Mutant 4 contains the following mutations that are distal from the active site: N396A, S398A, W399A. Mutant 3 was found to be inactive and therefore was not tested in the activity assay. Mutant 3 contains the following mutations in the S1' subsite of the active site: D572A, K575A, D577A.

Figure 6:
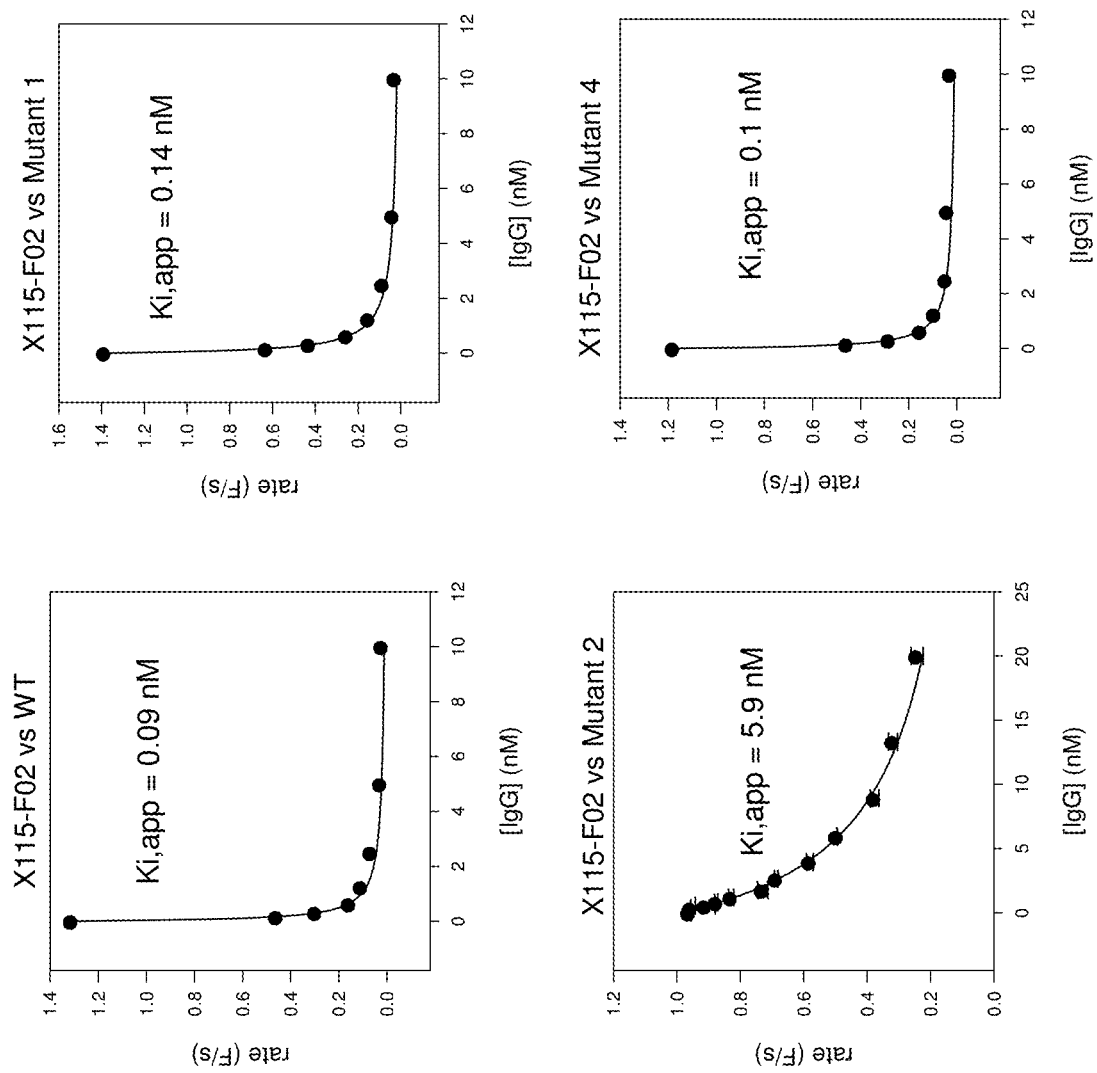
FIG. 6 is a series of graphs showing the apparent Ki ($K_{i,app}$) of mutant X115-F02 (see Table 2 below) against wild-type PKal and a number of PKal mutants.

The inhibitory activity of X115-F02 against the wild-type PKal and the mutants were carried out using the method described in Example 3 above and the $K_{i_{app}}$ values were determined. As shown in FIG. 6, the mutations in Mutant 1 and 4 did not significantly affect the potency of X115-F02 inhibition of plasma kallikrein. Surprisingly, the mutations in Mutant 2 reduced the potency approximately 65-fold. These results indicate that residues R551A, Q553A, Y555A, T558A, R560A and their adjacent residues might be important to the inhibitory activity of X115-F02 (DX-2930).

Example 5: Effect of DX-2944 in a Laser Induced Choroidal Neovascularization (Laser CNV) Disease Model—Study 3

DX-2944 as described herein was expressed and purified from an *E. coli* expression system. The Laser CNV model used in this study is an established rodent model of complications associated with human retinal diseases, such as age-related macular degeneration (AMD), retinal vein occlusions, and macular edema. The experimental design conducted is summarized below.

Experimental Design: Laser-induced Choroidal Neovascularization (CNV) in rats

Day 1: Bilateral Laser treatment to produce 3 lesions per eye

Figure 8:
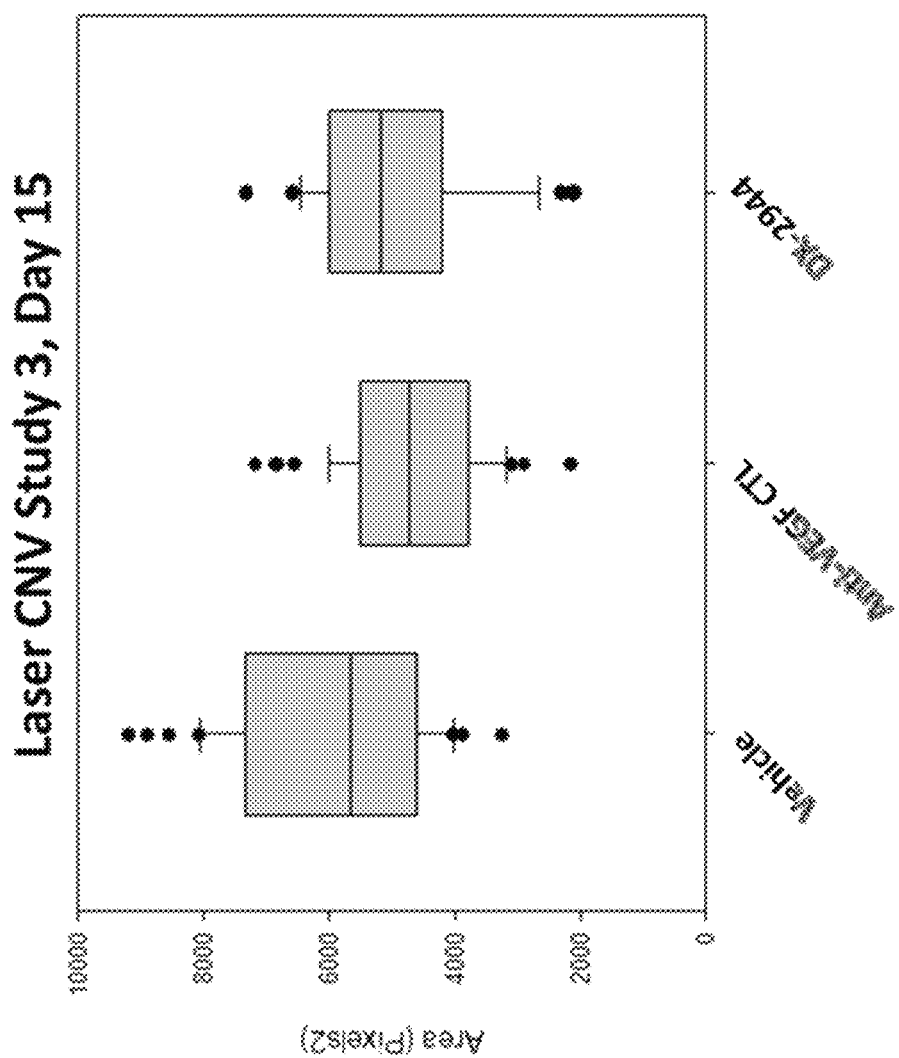
FIG. 8 shows the effect of DX-2944 compared with anti-VEGF positive control on laser CNV in brown Norway rats at day 15. The observed reduction in by fluorescein angiography signal in animals treated with an intra-ocular injection of an anti-VEGF antibody was comparable to reduction in signal observed with animals treated with DX-2944 (n=7, p<0.05 by t-test).
Figure 9:
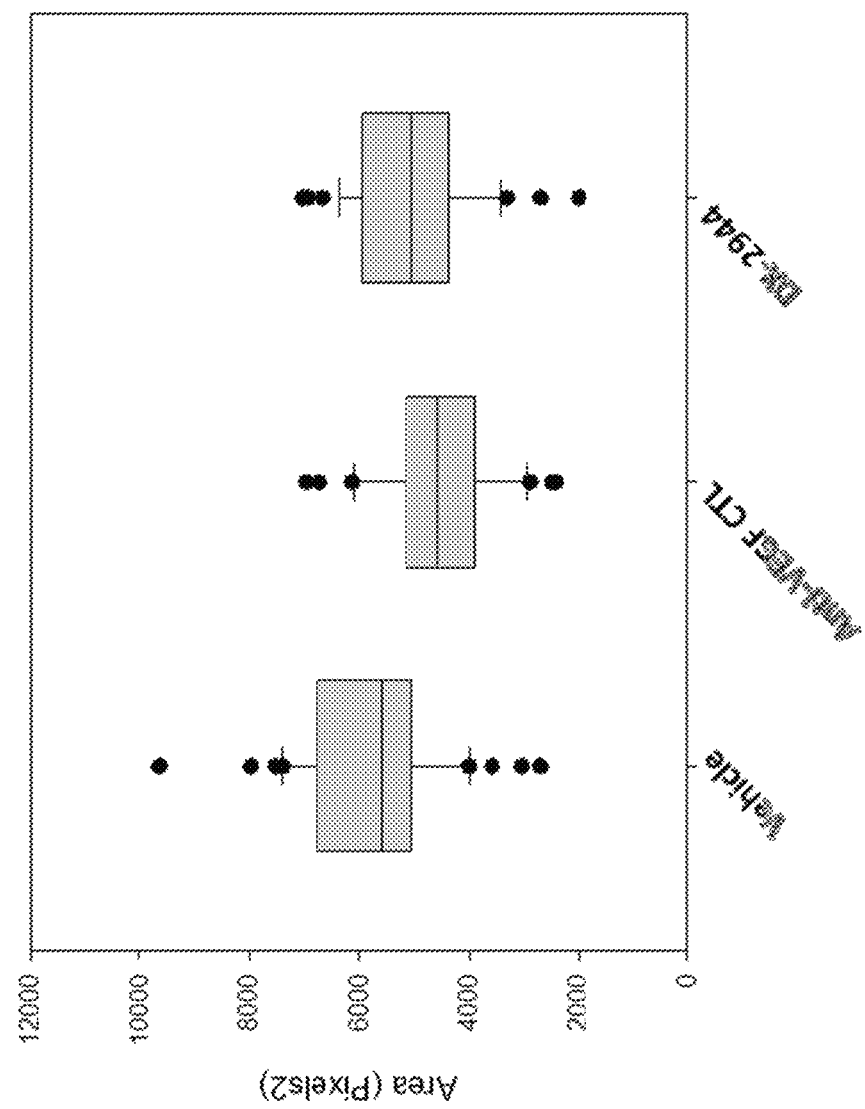
FIG. 9 shows the effect of DX-2944 compared with anti-VEGF positive control on laser CNV in brown Norway rats at day 22. The observed reduction in by fluorescein angiography signal in animals treated with an intra-ocular injection of an anti-VEGF antibody was comparable to reduction in signal observed with animals treated with DX-2944 (n=7, p<0.05 by t-test).

Day 3: Bilateral intravitreal injection of test agent, vehicle, and positive control Day 10: Bilateral intravitreal injection of test agent, vehicle, and positive control Day 15: In-vivo fluorescein angiography Day 22: In-vivo fluorescein angiography The results shown in FIG. 8 indicate that DX-2944 reduced observed CNV to approximately the same extent as the positive control (an anti-VEGF antibody) at Day 15 of the study. The fluorescein angiography mean signal for the anti-VEGF treated group was 4627 fluorescence units, which was similar to that observed for the DX-2944 treated group at 4917 fluorescence units. The results shown in FIG. 9 indicate that DX-2944 reduced observed CNV to approximately the same extent as the positive control at Day 22 of the study. The fluorescein angiography mean signal for the anti-VEGF treated group was 4551 fluorescence units, which was similar to that observed for the DX-2944 treated group at 5011 fluorescence units.

These results show that DX-2944 was effective to reduce CNV in the animal model, indicating that this antibody would be effective in treating human retinal diseases, such as age-related macular degeneration (AMD), retinal vein occlusions, and macular edema.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for treating a retinal disease in a subject, the method comprising:
 administering an effective amount of a composition comprising an antibody to the subject, wherein the antibody comprises:
 a heavy chain variable region comprising a complementarity determining region (CDR) 1 set forth as HYIMM (SEQ ID NO: 5), a CDR2 set forth as GIYSSGGITVYADSVKG (SEQ ID NO: 6), and a CDR3 set forth as RRTGVPRWDDFDI (SEQ ID NO: 45); and
 a light chain variable region comprising a CDR1 set forth as RASQSISSWLA (SEQ ID NO: 8), a CDR2 set forth as KASTLES (SEQ ID NO: 9), and a CDR3 set forth as QQYNTYWT (SEQ ID NO: 10);
 wherein the retinal disease is selected from the group consisting of diabetic macular edema (DME), age-related macular degeneration (AMD), and retinal vein occlusion (RVO).

2. The method of claim 1, wherein the retinal disease is diabetic macular edema.

3. The method of claim 1, wherein the antibody is a full-length antibody or an antigen-binding fragment thereof.

4. The method of claim 1, wherein the antibody is a Fab.

5. The method of claim 1, wherein the antibody is a human antibody or a humanized antibody.

6. The method of claim 1, wherein the composition is administered via intravitreal injection.

7. The method of claim 1, wherein the antibody is the only active agent administered to the subject for treating the retinal disease.

* * * * *

SEQUENCE LISTING

```
<160> NUMBER OF SEQ ID NOS: 59

<210> SEQ ID NO 1
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ile Met Met Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Ile Gly Val Pro Arg Arg Asp Glu Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

```
Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 2
<211> LENGTH: 213
<212> TYPE: PRT
<213> ORGANISM: Artificial Sequence
<220> FEATURE:
<223> OTHER INFORMATION: Synthetic Polypeptide

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

```
Cys Glu Val Thr His Gln Gly Leu Ser Ser Pro Val Thr Lys Ser Phe
        195                 200                 205

Asn Arg Gly Glu Cys
    210
```

<210> SEQ ID NO 3
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 3

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ile Met Met Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Ile Gly Val Pro Arg Arg Asp Glu Phe Asp Ile Trp
            100                 105                 110

Gly Gln Gly Thr Met Val Thr Val Ser Ser
        115                 120
```

<210> SEQ ID NO 4
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 4

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys
            100                 105
```

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

His Tyr Ile Met Met
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Gly Ile Tyr Ser Ser Gly Gly Ile Thr Val Tyr Ala Asp Ser Val Lys
1               5                   10                  15

Gly

<210> SEQ ID NO 7
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 7

Arg Arg Ile Gly Val Pro Arg Arg Asp Glu Phe Asp Ile
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 8

Arg Ala Ser Gln Ser Ile Ser Ser Trp Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 9

Lys Ala Ser Thr Leu Glu Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 10

Gln Gln Tyr Asn Thr Tyr Trp Thr
1               5

<210> SEQ ID NO 11
<211> LENGTH: 619
<212> TYPE: PRT
<213> ORGANISM: Homo sapiens

```
<400> SEQUENCE: 11

Gly Cys Leu Thr Gln Leu Tyr Glu Asn Ala Phe Phe Arg Gly Gly Asp
1               5                   10                  15

Val Ala Ser Met Tyr Thr Pro Asn Ala Gln Tyr Cys Gln Met Arg Cys
            20                  25                  30

Thr Phe His Pro Arg Cys Leu Leu Phe Ser Phe Leu Pro Ala Ser Ser
        35                  40                  45

Ile Asn Asp Met Glu Lys Arg Phe Gly Cys Phe Leu Lys Asp Ser Val
50                  55                  60

Thr Gly Thr Leu Pro Lys Val His Arg Thr Gly Ala Val Ser Gly His
65                  70                  75                  80

Ser Leu Lys Gln Cys Gly His Gln Ile Ser Ala Cys His Arg Asp Ile
                85                  90                  95

Tyr Lys Gly Val Asp Met Arg Gly Val Asn Phe Asn Val Ser Lys Val
                100                 105                 110

Ser Ser Val Glu Glu Cys Gln Lys Arg Cys Thr Ser Asn Ile Arg Cys
            115                 120                 125

Gln Phe Phe Ser Tyr Ala Thr Gln Thr Phe His Lys Ala Glu Tyr Arg
    130                 135                 140

Asn Asn Cys Leu Leu Lys Tyr Ser Pro Gly Gly Thr Pro Thr Ala Ile
145                 150                 155                 160

Lys Val Leu Ser Asn Val Glu Ser Gly Phe Ser Leu Lys Pro Cys Ala
                165                 170                 175

Leu Ser Glu Ile Gly Cys His Met Asn Ile Phe Gln His Leu Ala Phe
                180                 185                 190

Ser Asp Val Asp Val Ala Arg Val Leu Thr Pro Asp Ala Phe Val Cys
            195                 200                 205

Arg Thr Ile Cys Thr Tyr His Pro Asn Cys Leu Phe Phe Thr Phe Tyr
        210                 215                 220

Thr Asn Val Trp Lys Ile Glu Ser Gln Arg Asn Val Cys Leu Leu Lys
225                 230                 235                 240

Thr Ser Glu Ser Gly Thr Pro Ser Ser Ser Thr Pro Gln Glu Asn Thr
                245                 250                 255

Ile Ser Gly Tyr Ser Leu Leu Thr Cys Lys Arg Thr Leu Pro Glu Pro
                260                 265                 270

Cys His Ser Lys Ile Tyr Pro Gly Val Asp Phe Gly Gly Glu Glu Leu
            275                 280                 285

Asn Val Thr Phe Val Lys Gly Val Asn Val Cys Gln Glu Thr Cys Thr
        290                 295                 300

Lys Met Ile Arg Cys Gln Phe Phe Thr Tyr Ser Leu Leu Pro Glu Asp
305                 310                 315                 320

Cys Lys Glu Glu Lys Cys Lys Cys Phe Leu Arg Leu Ser Met Asp Gly
                325                 330                 335

Ser Pro Thr Arg Ile Ala Tyr Gly Thr Gln Gly Ser Ser Gly Tyr Ser
                340                 345                 350

Leu Arg Leu Cys Asn Thr Gly Asp Asn Ser Val Cys Thr Thr Lys Thr
            355                 360                 365

Ser Thr Arg Ile Val Gly Gly Thr Asn Ser Ser Trp Gly Glu Trp Pro
        370                 375                 380

Trp Gln Val Ser Leu Gln Val Lys Leu Thr Ala Gln Arg His Leu Cys
385                 390                 395                 400

Gly Gly Ser Leu Ile Gly His Gln Trp Val Leu Thr Ala Ala His Cys
                405                 410                 415
```

```
Phe Asp Gly Leu Pro Leu Gln Asp Val Trp Arg Ile Tyr Ser Gly Ile
            420                 425                 430

Leu Asn Leu Ser Asp Ile Thr Lys Asp Thr Pro Phe Ser Gln Ile Lys
            435                 440                 445

Glu Ile Ile Ile His Gln Asn Tyr Lys Val Ser Glu Gly Asn His Asp
450                 455                 460

Ile Ala Leu Ile Lys Leu Gln Ala Pro Leu Asn Tyr Thr Glu Phe Gln
465                 470                 475                 480

Lys Pro Ile Ser Leu Pro Ser Lys Gly Asp Thr Ser Thr Ile Tyr Thr
                485                 490                 495

Asn Cys Trp Val Thr Gly Trp Gly Phe Ser Lys Glu Lys Gly Glu Ile
            500                 505                 510

Gln Asn Ile Leu Gln Lys Val Asn Ile Pro Leu Val Thr Asn Glu Glu
            515                 520                 525

Cys Gln Lys Arg Tyr Gln Asp Tyr Lys Ile Thr Gln Arg Met Val Cys
            530                 535                 540

Ala Gly Tyr Lys Glu Gly Gly Lys Asp Ala Cys Lys Gly Asp Ser Gly
545                 550                 555                 560

Gly Pro Leu Val Cys Lys His Asn Gly Met Trp Arg Leu Val Gly Ile
                565                 570                 575

Thr Ser Trp Gly Glu Gly Cys Ala Arg Arg Glu Gln Pro Gly Val Tyr
            580                 585                 590

Thr Lys Val Ala Glu Tyr Met Asp Trp Ile Leu Glu Lys Thr Gln Ser
            595                 600                 605

Ser Asp Gly Lys Ala Gln Met Gln Ser Pro Ala
            610                 615

<210> SEQ ID NO 12
<211> LENGTH: 638
<212> TYPE: PRT
<213> ORGANISM: Homo sapiens

<400> SEQUENCE: 12

Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
            20                  25                  30

Gly Gly Asp Val Ala Ser Met Tyr Thr Pro Asn Ala Gln Tyr Cys Gln
            35                  40                  45

Met Arg Cys Thr Phe His Pro Arg Cys Leu Leu Phe Ser Phe Leu Pro
50                  55                  60

Ala Ser Ser Ile Asn Asp Met Glu Lys Arg Phe Gly Cys Phe Leu Lys
65                  70                  75                  80

Asp Ser Val Thr Gly Thr Leu Pro Lys Val His Arg Thr Gly Ala Val
                85                  90                  95

Ser Gly His Ser Leu Lys Gln Cys Gly His Gln Ile Ser Ala Cys His
            100                 105                 110

Arg Asp Ile Tyr Lys Gly Val Asp Met Arg Gly Val Asn Phe Asn Val
            115                 120                 125

Ser Lys Val Ser Ser Val Glu Glu Cys Gln Lys Arg Cys Thr Ser Asn
            130                 135                 140

Ile Arg Cys Gln Phe Phe Ser Tyr Ala Thr Gln Thr Phe His Lys Ala
145                 150                 155                 160

Glu Tyr Arg Asn Asn Cys Leu Leu Lys Tyr Ser Pro Gly Gly Thr Pro
```

-continued

```
                165                 170                 175
Thr Ala Ile Lys Val Leu Ser Asn Val Glu Ser Gly Phe Ser Leu Lys
                180                 185                 190
Pro Cys Ala Leu Ser Glu Ile Gly Cys His Met Asn Ile Phe Gln His
                195                 200                 205
Leu Ala Phe Ser Asp Val Asp Val Ala Arg Val Leu Thr Pro Asp Ala
                210                 215                 220
Phe Val Cys Arg Thr Ile Cys Thr Tyr His Pro Asn Cys Leu Phe Phe
225                 230                 235                 240
Thr Phe Tyr Thr Asn Val Trp Lys Ile Glu Ser Gln Arg Asn Val Cys
                245                 250                 255
Leu Leu Lys Thr Ser Glu Ser Gly Thr Pro Ser Ser Thr Pro Gln
                260                 265                 270
Glu Asn Thr Ile Ser Gly Tyr Ser Leu Leu Thr Cys Lys Arg Thr Leu
                275                 280                 285
Pro Glu Pro Cys His Ser Lys Ile Tyr Pro Gly Val Asp Phe Gly Gly
                290                 295                 300
Glu Glu Leu Asn Val Thr Phe Val Lys Gly Val Asn Val Cys Gln Glu
305                 310                 315                 320
Thr Cys Thr Lys Met Ile Arg Cys Gln Phe Phe Thr Tyr Ser Leu Leu
                325                 330                 335
Pro Glu Asp Cys Lys Glu Lys Cys Lys Cys Phe Leu Arg Leu Ser
                340                 345                 350
Met Asp Gly Ser Pro Thr Arg Ile Ala Tyr Gly Thr Gln Gly Ser Ser
                355                 360                 365
Gly Tyr Ser Leu Arg Leu Cys Asn Thr Gly Asp Asn Ser Val Cys Thr
                370                 375                 380
Thr Lys Thr Ser Thr Arg Ile Val Gly Gly Thr Asn Ser Ser Trp Gly
385                 390                 395                 400
Glu Trp Pro Trp Gln Val Ser Leu Gln Val Lys Leu Thr Ala Gln Arg
                405                 410                 415
His Leu Cys Gly Gly Ser Leu Ile Gly His Gln Trp Val Leu Thr Ala
                420                 425                 430
Ala His Cys Phe Asp Gly Leu Pro Leu Gln Asp Val Trp Arg Ile Tyr
                435                 440                 445
Ser Gly Ile Leu Asn Leu Ser Asp Ile Thr Lys Asp Thr Pro Phe Ser
                450                 455                 460
Gln Ile Lys Glu Ile Ile Ile His Gln Asn Tyr Lys Val Ser Glu Gly
465                 470                 475                 480
Asn His Asp Ile Ala Leu Ile Lys Leu Gln Ala Pro Leu Asn Tyr Thr
                485                 490                 495
Glu Phe Gln Lys Pro Ile Cys Leu Pro Ser Lys Gly Asp Thr Ser Thr
                500                 505                 510
Ile Tyr Thr Asn Cys Trp Val Thr Gly Trp Gly Phe Ser Lys Glu Lys
                515                 520                 525
Gly Glu Ile Gln Asn Ile Leu Gln Lys Val Asn Ile Pro Leu Val Thr
                530                 535                 540
Asn Glu Glu Cys Gln Lys Arg Tyr Gln Asp Tyr Lys Ile Thr Gln Arg
545                 550                 555                 560
Met Val Cys Ala Gly Tyr Lys Glu Gly Gly Lys Asp Ala Cys Lys Gly
                565                 570                 575
Asp Ser Gly Gly Pro Leu Val Cys Lys His Asn Gly Met Trp Arg Leu
                580                 585                 590
```

-continued

Val Gly Ile Thr Ser Trp Gly Glu Gly Cys Ala Arg Arg Glu Gln Pro
        595                 600                 605

Gly Val Tyr Thr Lys Val Ala Glu Tyr Met Asp Trp Ile Leu Glu Lys
610                 615                 620

Thr Gln Ser Ser Asp Gly Lys Ala Gln Met Gln Ser Pro Ala
625                 630                 635

<210> SEQ ID NO 13
<211> LENGTH: 638
<212> TYPE: PRT
<213> ORGANISM: Rattus norvegicus

<400> SEQUENCE: 13

Met Ile Leu Phe Lys Gln Val Gly Tyr Phe Val Ser Leu Phe Ala Thr
1               5                   10                  15

Val Ser Cys Gly Cys Leu Ser Gln Leu Tyr Ala Asn Thr Phe Phe Arg
            20                  25                  30

Gly Gly Asp Leu Ala Ala Ile Tyr Thr Pro Asp Ala Gln His Cys Gln
        35                  40                  45

Lys Met Cys Thr Phe His Pro Arg Cys Leu Leu Phe Ser Phe Leu Ala
50                  55                  60

Val Ser Pro Thr Lys Glu Thr Asp Lys Arg Phe Gly Cys Phe Met Lys
65                  70                  75                  80

Glu Ser Ile Thr Gly Thr Leu Pro Arg Ile His Arg Thr Gly Ala Ile
                85                  90                  95

Ser Gly His Ser Leu Lys Gln Cys Gly His Gln Leu Ser Ala Cys His
            100                 105                 110

Gln Asp Ile Tyr Glu Gly Leu Asp Met Arg Gly Ser Asn Phe Asn Ile
        115                 120                 125

Ser Lys Thr Asp Ser Ile Glu Glu Cys Gln Lys Leu Cys Thr Asn Asn
130                 135                 140

Ile His Cys Gln Phe Phe Thr Tyr Ala Thr Lys Ala Phe His Arg Pro
145                 150                 155                 160

Glu Tyr Arg Lys Ser Cys Leu Leu Lys Arg Ser Ser Ser Gly Thr Pro
                165                 170                 175

Thr Ser Ile Lys Pro Val Asp Asn Leu Val Ser Gly Phe Ser Leu Lys
            180                 185                 190

Ser Cys Ala Leu Ser Glu Ile Gly Cys Pro Met Asp Ile Phe Gln His
        195                 200                 205

Phe Ala Phe Ala Asp Leu Asn Val Ser His Val Thr Pro Asp Ala
210                 215                 220

Phe Val Cys Arg Thr Val Cys Thr Phe His Pro Asn Cys Leu Phe Phe
225                 230                 235                 240

Thr Phe Tyr Thr Asn Glu Trp Glu Thr Glu Ser Gln Arg Asn Val Cys
                245                 250                 255

Phe Leu Lys Thr Ser Lys Ser Gly Arg Pro Ser Pro Ile Ile Gln
            260                 265                 270

Glu Asn Ala Val Ser Gly Tyr Ser Leu Phe Thr Cys Arg Lys Ala Arg
        275                 280                 285

Pro Glu Pro Cys His Phe Lys Ile Tyr Ser Gly Val Ala Phe Glu Gly
        290                 295                 300

Glu Glu Leu Asn Ala Thr Phe Val Gln Gly Ala Asp Ala Cys Gln Glu
305                 310                 315                 320

Thr Cys Thr Lys Thr Ile Arg Cys Gln Phe Phe Thr Tyr Ser Leu Leu

```
                        325                 330                 335
        Pro Gln Asp Cys Lys Ala Glu Gly Cys Lys Cys Ser Leu Arg Leu Ser
                        340                 345                 350

Thr Asp Gly Ser Pro Thr Arg Ile Thr Tyr Glu Ala Gln Gly Ser Ser
                        355                 360                 365

Gly Tyr Ser Leu Arg Leu Cys Lys Val Val Glu Ser Ser Asp Cys Thr
                        370                 375                 380

Thr Lys Ile Asn Ala Arg Ile Val Gly Thr Asn Ser Ser Leu Gly
        385                 390                 395                 400

Glu Trp Pro Trp Gln Val Ser Leu Gln Val Lys Leu Val Ser Gln Asn
                        405                 410                 415

His Met Cys Gly Gly Ser Ile Ile Gly Arg Gln Trp Ile Leu Thr Ala
                        420                 425                 430

Ala His Cys Phe Asp Gly Ile Pro Tyr Pro Asp Val Trp Arg Ile Tyr
                        435                 440                 445

Gly Gly Ile Leu Asn Leu Ser Glu Ile Thr Asn Lys Thr Pro Phe Ser
                        450                 455                 460

Ser Ile Lys Glu Leu Ile Ile His Gln Lys Tyr Lys Met Ser Glu Gly
        465                 470                 475                 480

Ser Tyr Asp Ile Ala Leu Ile Lys Leu Gln Thr Pro Leu Asn Tyr Thr
                        485                 490                 495

Glu Phe Gln Lys Pro Ile Cys Leu Pro Ser Lys Ala Asp Thr Asn Thr
                        500                 505                 510

Ile Tyr Thr Asn Cys Trp Val Thr Gly Trp Gly Tyr Thr Lys Glu Arg
                        515                 520                 525

Gly Glu Thr Gln Asn Ile Leu Gln Lys Ala Thr Ile Pro Leu Val Pro
                        530                 535                 540

Asn Glu Glu Cys Gln Lys Lys Tyr Arg Asp Tyr Val Ile Thr Lys Gln
        545                 550                 555                 560

Met Ile Cys Ala Gly Tyr Lys Glu Gly Gly Ile Asp Ala Cys Lys Gly
                        565                 570                 575

Asp Ser Gly Gly Pro Leu Val Cys Lys His Ser Gly Arg Trp Gln Leu
                        580                 585                 590

Val Gly Ile Thr Ser Trp Gly Glu Gly Cys Ala Arg Lys Glu Gln Pro
                        595                 600                 605

Gly Val Tyr Thr Lys Val Ala Glu Tyr Ile Asp Trp Ile Leu Glu Lys
                        610                 615                 620

Ile Gln Ser Ser Lys Glu Arg Ala Leu Glu Thr Ser Pro Ala
        625                 630                 635

<210> SEQ ID NO 14
<211> LENGTH: 638
<212> TYPE: PRT
<213> ORGANISM: Mus musculus

<400> SEQUENCE: 14

Met Ile Leu Phe Asn Arg Val Gly Tyr Phe Val Ser Leu Phe Ala Thr
        1               5                   10                  15

Val Ser Cys Gly Cys Met Thr Gln Leu Tyr Lys Asn Thr Phe Arg
                        20                  25                  30

Gly Gly Asp Leu Ala Ala Ile Tyr Thr Pro Asp Ala Gln Tyr Cys Gln
                        35                  40                  45

Lys Met Cys Thr Phe His Pro Arg Cys Leu Leu Phe Ser Phe Leu Ala
                        50                  55                  60
```

```
Val Thr Pro Pro Lys Glu Thr Asn Lys Arg Phe Gly Cys Phe Met Lys
 65                  70                  75                  80

Glu Ser Ile Thr Gly Thr Leu Pro Arg Ile His Arg Thr Gly Ala Ile
                 85                  90                  95

Ser Gly His Ser Leu Lys Gln Cys Gly His Gln Ile Ser Ala Cys His
            100                 105                 110

Arg Asp Ile Tyr Lys Gly Leu Asp Met Arg Gly Ser Asn Phe Asn Ile
            115                 120                 125

Ser Lys Thr Asp Asn Ile Glu Glu Cys Gln Lys Leu Cys Thr Asn Asn
        130                 135                 140

Phe His Cys Gln Phe Phe Thr Tyr Ala Thr Ser Ala Phe Tyr Arg Pro
145                 150                 155                 160

Glu Tyr Arg Lys Lys Cys Leu Leu Lys His Ser Ala Ser Gly Thr Pro
                165                 170                 175

Thr Ser Ile Lys Ser Ala Asp Asn Leu Val Ser Gly Phe Ser Leu Lys
            180                 185                 190

Ser Cys Ala Leu Ser Glu Ile Gly Cys Pro Met Asp Ile Phe Gln His
            195                 200                 205

Ser Ala Phe Ala Asp Leu Asn Val Ser Gln Val Ile Thr Pro Asp Ala
210                 215                 220

Phe Val Cys Arg Thr Ile Cys Thr Phe His Pro Asn Cys Leu Phe Phe
225                 230                 235                 240

Thr Phe Tyr Thr Asn Glu Trp Glu Thr Glu Ser Gln Arg Asn Val Cys
                245                 250                 255

Phe Leu Lys Thr Ser Lys Ser Gly Arg Pro Ser Pro Ile Pro Gln
            260                 265                 270

Glu Asn Ala Ile Ser Gly Tyr Ser Leu Leu Thr Cys Arg Lys Thr Arg
        275                 280                 285

Pro Glu Pro Cys His Ser Lys Ile Tyr Ser Gly Val Asp Phe Glu Gly
        290                 295                 300

Glu Glu Leu Asn Val Thr Phe Val Gln Gly Ala Asp Val Cys Gln Glu
305                 310                 315                 320

Thr Cys Thr Lys Thr Ile Arg Cys Gln Phe Phe Ile Tyr Ser Leu Leu
                325                 330                 335

Pro Gln Asp Cys Lys Glu Glu Gly Cys Lys Cys Ser Leu Arg Leu Ser
            340                 345                 350

Thr Asp Gly Ser Pro Thr Arg Ile Thr Tyr Gly Met Gln Gly Ser Ser
        355                 360                 365

Gly Tyr Ser Leu Arg Leu Cys Lys Leu Val Asp Ser Pro Asp Cys Thr
370                 375                 380

Thr Lys Ile Asn Ala Arg Ile Val Gly Gly Thr Asn Ala Ser Leu Gly
385                 390                 395                 400

Glu Trp Pro Trp Gln Val Ser Leu Gln Val Lys Leu Val Ser Gln Thr
                405                 410                 415

His Leu Cys Gly Gly Ser Ile Ile Gly Arg Gln Trp Val Leu Thr Ala
            420                 425                 430

Ala His Cys Phe Asp Gly Ile Pro Tyr Pro Asp Val Trp Arg Ile Tyr
        435                 440                 445

Gly Gly Ile Leu Ser Leu Ser Glu Ile Thr Lys Glu Thr Pro Ser Ser
        450                 455                 460

Arg Ile Lys Glu Leu Ile Ile His Gln Glu Tyr Lys Val Ser Glu Gly
465                 470                 475                 480

Asn Tyr Asp Ile Ala Leu Ile Lys Leu Gln Thr Pro Leu Asn Tyr Thr
```

```
                485                 490                 495
Glu Phe Gln Lys Pro Ile Cys Leu Pro Ser Lys Ala Asp Thr Asn Thr
            500                 505                 510

Ile Tyr Thr Asn Cys Trp Val Thr Gly Trp Gly Tyr Thr Lys Glu Gln
        515                 520                 525

Gly Glu Thr Gln Asn Ile Leu Gln Lys Ala Thr Ile Pro Leu Val Pro
    530                 535                 540

Asn Glu Glu Cys Gln Lys Lys Tyr Arg Asp Tyr Val Ile Asn Lys Gln
545                 550                 555                 560

Met Ile Cys Ala Gly Tyr Lys Glu Gly Gly Thr Asp Ala Cys Lys Gly
                565                 570                 575

Asp Ser Gly Gly Pro Leu Val Cys Lys His Ser Gly Arg Trp Gln Leu
            580                 585                 590

Val Gly Ile Thr Ser Trp Gly Glu Gly Cys Gly Arg Lys Asp Gln Pro
        595                 600                 605

Gly Val Tyr Thr Lys Val Ser Glu Tyr Met Asp Trp Ile Leu Glu Lys
    610                 615                 620

Thr Gln Ser Ser Asp Val Arg Ala Leu Glu Thr Ser Ser Ala
625                 630                 635
```

<210> SEQ ID NO 15
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is Arg or Gln
<220> FEATURE:
<221> NAME/KEY: MISC_FEATURE
<222> LOCATION: (3)..(3)
<223> OTHER INFORMATION: Xaa is Thr, Ile, Arg, Ser, or Pro
<220> FEATURE:
<221> NAME/KEY: MISC_FEATURE
<222> LOCATION: (5)..(5)
<223> OTHER INFORMATION: Xaa is Val, Ile, or Leu
<220> FEATURE:
<221> NAME/KEY: MISC_FEATURE
<222> LOCATION: (8)..(8)
<223> OTHER INFORMATION: Xaa is Arg or Trp
<220> FEATURE:
<221> NAME/KEY: MISC_FEATURE
<222> LOCATION: (9)..(9)
<223> OTHER INFORMATION: Xaa is Asp or Asn
<220> FEATURE:
<221> NAME/KEY: MISC_FEATURE
<222> LOCATION: (10)..(10)
<223> OTHER INFORMATION: Xaa is Ala, Ser, Asp, Glu, or Val
<220> FEATURE:
<221> NAME/KEY: MISC_FEATURE
<222> LOCATION: (11)..(11)
<223> OTHER INFORMATION: Xaa is Phe or Leu
<220> FEATURE:
<221> NAME/KEY: MISC_FEATURE
<222> LOCATION: (12)..(12)
<223> OTHER INFORMATION: Xaa is Asp, Glu, or Asn
<220> FEATURE:
<221> NAME/KEY: MISC_FEATURE
<222> LOCATION: (13)..(13)
<223> OTHER INFORMATION: Xaa is Ile, Asn, Met, or Ser

<400> SEQUENCE: 15

Xaa Arg Xaa Gly Xaa Pro Arg Xaa Xaa Xaa Xaa Xaa Xaa
1               5                   10

```
<210> SEQ ID NO 16
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys
            100                 105

<210> SEQ ID NO 17
<211> LENGTH: 102
<212> TYPE: PRT
<213> ORGANISM: Artificial Sequence
<220> FEATURE:
<223> OTHER INFORMATION: Synthetic Polypeptide

<400> SEQUENCE: 17

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Leu Leu Ile Tyr
        35                  40                  45

Ala Ser Leu Glu Ser Gly Val Pro Ser Arg Phe Ser Gly Ser Gly Ser
    50                  55                  60

Gly Thr Glu Phe Thr Leu Thr Ile Ser Ser Leu Gln Pro Asp Asp Phe
65                  70                  75                  80

Ala Thr Tyr Tyr Cys Gln Gln Tyr Asn Tyr Trp Thr Phe Gly Gln Gly
                85                  90                  95

Thr Lys Val Glu Ile Lys
            100

<210> SEQ ID NO 18
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 18

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Asp Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Trp Thr
                 85                  90                  95

Phe Gly Gln Gly Thr Lys Val Glu Ile Lys
            100                 105
```

<210> SEQ ID NO 19
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 19

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Ile Met Met Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Tyr Arg Arg Thr Gly Ile Pro Arg Arg Asp Ala Phe Asp Ile Trp
            100                 105                 110

Gly Gln Gly Thr Met Val Thr Val Ser Ser
            115                 120
```

<210> SEQ ID NO 20
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 20

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Met
            20                  25                  30

Trp Val Arg Gln Ala Pro Gly Lys Gly Leu Glu Trp Val Ser Ile Ser
        35                  40                  45

Gly Gly Thr Tyr Ala Asp Ser Val Lys Gly Arg Phe Thr Ile Ser Arg
 50                  55                  60

Asp Asn Ser Lys Asn Thr Leu Tyr Leu Gln Met Asn Ser Leu Arg Ala
 65                  70                  75                  80

Glu Asp Thr Ala Val Tyr Tyr Cys Ala Ala Phe Asp Ile Trp Gly Gln
                 85                  90                  95

Gly Thr Met Val Thr Val Ser Ser
            100
```

```
<210> SEQ ID NO 21
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Phe Asp Ile Trp Gly Gln Gly Thr Met Val Thr Val Ser
            100                 105                 110

Ser

<210> SEQ ID NO 22
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 22

Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
        35                  40                  45

Leu Pro Leu Gln Asp Val Trp Arg Ile Tyr Ser Gly Ile Leu Asn Leu
    50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Cys Leu Pro Ser Lys Gly Asp Thr Ser Thr Ile Tyr Thr Asn Cys Trp
        115                 120                 125

Val Thr Gly Trp Gly Phe Ser Lys Glu Lys Gly Glu Ile Gln Asn Ile
    130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Asp Ala Cys Lys Gly Asp Ser Gly Gly Pro Leu
            180                 185                 190

Val Cys Lys His Asn Gly Met Trp Arg Leu Val Gly Ile Thr Ser Trp
```

```
                      195                 200                 205
Gly Glu Gly Cys Ala Arg Arg Glu Gln Pro Gly Val Tyr Thr Lys Val
            210                 215                 220
Ala Glu Tyr Met Asp Trp Ile Leu Glu Lys Thr Gln Ser Ser Asp Gly
225                 230                 235                 240
Lys Ala Gln Met Gln Ser Pro Ala
                245

<210> SEQ ID NO 23
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 23

Ile Val Gly Gly Thr Asn Ser Ser Trp Gly Glu Trp Pro Trp Gln Val
1               5                   10                  15
Ser Leu Gln Val Lys Leu Thr Ala Gln Arg His Leu Cys Gly Gly Ser
                20                  25                  30
Leu Ile Gly His Gln Trp Val Leu Thr Ala Ala His Cys Phe Asp Gly
            35                  40                  45
Leu Pro Leu Gln Asp Val Trp Arg Ile Tyr Ser Gly Ile Leu Asn Leu
        50                  55                  60
Ser Asp Ile Thr Lys Asp Thr Pro Phe Ser Gln Ile Lys Glu Ile Ile
65                  70                  75                  80
Ile His Gln Asn Tyr Lys Val Ala Glu Gly His Asp Ile Ala Leu
                85                  90                  95
Ile Lys Leu Gln Ala Pro Leu Asn Tyr Thr Glu Phe Gln Lys Pro Ile
            100                 105                 110
Ser Leu Pro Ala Ala Gly Asp Thr Ser Thr Ile Tyr Thr Asn Cys Trp
        115                 120                 125
Val Thr Gly Trp Gly Phe Ser Lys Glu Lys Gly Glu Ile Gln Asn Ile
130                 135                 140
Leu Gln Lys Val Asn Ile Pro Leu Val Thr Asn Glu Glu Cys Gln Lys
145                 150                 155                 160
Arg Tyr Gln Asp Tyr Lys Ile Thr Gln Arg Met Val Cys Ala Gly Tyr
                165                 170                 175
Lys Glu Gly Gly Lys Asp Ala Cys Lys Gly Asp Ser Gly Gly Pro Leu
            180                 185                 190
Val Cys Lys His Asn Gly Met Trp Arg Leu Val Gly Ile Thr Ser Trp
        195                 200                 205
Gly Glu Gly Cys Ala Arg Arg Glu Gln Pro Gly Val Tyr Thr Lys Val
    210                 215                 220
Ala Glu Tyr Met Asp Trp Ile Leu Glu Lys Thr Gln Ser Ser Asp Gly
225                 230                 235                 240
Lys Ala Gln Met Gln Ser Pro Ala
                245

<210> SEQ ID NO 24
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 24
```

Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
        35                  40                  45

Leu Pro Leu Gln Asp Val Trp Arg Ile Tyr Ser Gly Ile Leu Asn Leu
    50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Ser Leu Pro Ser Lys Gly Asp Thr Ser Thr Ile Tyr Thr Asn Cys Trp
        115                 120                 125

Val Thr Gly Trp Gly Phe Ser Lys Glu Lys Gly Glu Ile Gln Asn Ile
    130                 135                 140

Leu Gln Lys Val Asn Ile Pro Leu Val Thr Asn Glu Glu Cys Gln Lys
145                 150                 155                 160

Ala Tyr Ala Asp Ala Lys Ile Ala Gln Ala Met Val Cys Ala Gly Tyr
                165                 170                 175

Lys Glu Gly Gly Lys Asp Ala Cys Lys Gly Asp Ser Gly Gly Pro Leu
            180                 185                 190

Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
    210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
                245

<210> SEQ ID NO 25
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 25

Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
        35                  40                  45

Leu Pro Leu Gln Asp Val Trp Arg Ile Tyr Ser Gly Ile Leu Asn Leu
    50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Ser Leu Pro Ser Lys Gly Asp Thr Ser Thr Ile Tyr Thr Asn Cys Trp
            115                 120                 125

Val Thr Gly Trp Gly Phe Ser Lys Glu Lys Gly Glu Ile Gln Asn Ile
        130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Ala Ala Cys Ala Gly Ala Ser Gly Gly Pro Leu
            180                 185                 190

Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
            245

<210> SEQ ID NO 26
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 26

Ile Val Gly Gly Thr Ala Ser Ala Ala Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
        35                  40                  45

Leu Pro Leu Gln Asp Val Trp Arg Ile Tyr Ser Gly Ile Leu Asn Leu
    50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Ser Leu Pro Ser Lys Gly Asp Thr Ser Thr Ile Tyr Thr Asn Cys Trp
            115                 120                 125

Val Thr Gly Trp Gly Phe Ser Lys Glu Lys Gly Glu Ile Gln Asn Ile
        130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Asp Ala Cys Lys Gly Asp Ser Gly Gly Pro Leu
            180                 185                 190

Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
            245

<210> SEQ ID NO 27
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 27

Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
        35                  40                  45

Leu Pro Leu Gln Asp Val Trp Arg Ile Tyr Ser Gly Ile Leu Asn Leu
    50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Ser Leu Pro Ser Lys Gly Asp Thr Ser Thr Ile Tyr Thr Asn Cys Trp
        115                 120                 125

Val Thr Gly Trp Gly Phe Ser Lys Glu Lys Gly Glu Ile Gln Asn Ile
    130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Asp Ala Cys Lys Gly Asp Ser Gly Gly Pro Leu
            180                 185                 190

Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
    210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
            245

<210> SEQ ID NO 28
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 28

Arg Arg Thr Gly Ile Pro Arg Arg Asp Ala Phe Asp Ile
1               5                   10

<210> SEQ ID NO 29

```
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 29

Arg Arg Arg Gly Ile Pro Arg Arg Asp Ala Phe Asp Ile
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 30

Arg Arg Ser Gly Ile Pro Arg Arg Asp Ala Phe Asp Ile
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 31

Arg Arg Thr Gly Ile Pro Arg Trp Asp Ala Phe Asp Ile
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 32

Arg Arg Thr Gly Ile Pro Arg Arg Asp Val Phe Asp Ile
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 33

Arg Arg Thr Gly Ile Pro Arg Arg Asp Ala Phe Glu Ile
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 34

Arg Arg Thr Gly Ile Pro Arg Arg Asp Ala Phe Asp Asn
1               5                   10

<210> SEQ ID NO 35
<211> LENGTH: 13
```

<212> TYPE: PRT
<213> ORGANISM: Artificial Sequence
<220> FEATURE:
<223> OTHER INFORMATION: Synthetic Polypeptide

<400> SEQUENCE: 35

Arg Arg Thr Gly Ile Pro Arg Arg Asp Ala Phe Asp Ser
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 36

Arg Arg Thr Gly Val Pro Arg Arg Asp Ala Phe Asp Ile
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 37

Arg Arg Thr Gly Val Pro Arg Arg Asp Val Phe Asp Ile
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 38

Arg Arg Thr Gly Val Pro Arg Arg Asp Ala Leu Asp Asn
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 39

Arg Arg Thr Gly Val Pro Arg Arg Asp Ala Phe Asp Asn
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 40

Arg Arg Thr Gly Val Pro Arg Arg Asn Ala Phe Asp Asn
1               5                   10

<210> SEQ ID NO 41
<211> LENGTH: 13
<212> TYPE: PRT

<213> ORGANISM: Artificial Sequence
<220> FEATURE:
<223> OTHER INFORMATION: Synthetic Polypeptide

<400> SEQUENCE: 41

Arg Arg Thr Gly Val Pro Arg Trp Asp Ala Phe Asp Ile
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 42

Arg Arg Thr Gly Val Pro Arg Arg Asp Ser Phe Asp Ile
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 43

Arg Arg Thr Gly Val Pro Arg Arg Asp Ser Phe Glu Ile
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 44

Gln Arg Thr Gly Val Pro Arg Arg Asp Ser Phe Asn Ile
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 45

Arg Arg Thr Gly Val Pro Arg Trp Asp Asp Phe Asp Ile
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 46

Arg Arg Thr Gly Val Pro Arg Arg Asp Glu Phe Asp Ile
1               5                   10

<210> SEQ ID NO 47
<211> LENGTH: 13
<212> TYPE: PRT
<213> ORGANISM: Artificial Sequence

```
<220> FEATURE:
<223> OTHER INFORMATION: Synthetic Polypeptide

<400> SEQUENCE: 47

Arg Arg Pro Gly Val Pro Arg Arg Asp Ala Phe Asp Ile
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 48

Arg Arg Ser Gly Val Pro Arg Arg Asp Ala Phe Asp Ile
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 49

Arg Arg Arg Gly Val Pro Arg Arg Asp Asp Phe Asp Ile
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 50

Arg Arg Ile Gly Val Pro Arg Arg Asp Ala Phe Asp Ile
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 51

Arg Arg Ile Gly Val Pro Arg Arg Asp Ser Phe Asp Ile
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 52

Arg Arg Ile Gly Val Pro Arg Arg Asp Ser Phe Asp Met
1               5                   10

<210> SEQ ID NO 53
<211> LENGTH: 13
<212> TYPE: PRT
<213> ORGANISM: Artificial Sequence
<220> FEATURE:
```

```
<223> OTHER INFORMATION: Synthetic Polypeptide

<400> SEQUENCE: 53

Arg Arg Ile Gly Val Pro Arg Arg Asp Asp Phe Asp Ile
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 54

Arg Arg Ile Gly Ile Pro Arg Arg Asp Ala Phe Asp Ile
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 55

Arg Arg Ile Gly Ile Pro Arg Arg Asp Glu Phe Asp Ile
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 56

Arg Arg Thr Gly Ala Pro Arg Arg Asp Ala Phe Asp Ile
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 57

Arg Arg Thr Gly Ser Pro Arg Arg Asp Ala Phe Asp Ile
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 58

Arg Arg Thr Gly Leu Pro Arg Arg Asp Ala Phe Asp Ile
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic Polypeptide
```

```
<400> SEQUENCE: 59

Arg Arg Thr Gly Ile Pro Arg Arg Asp Glu Phe Asp Ile
1               5                   10
```